(12) United States Patent
Perry et al.

(10) Patent No.: US 7,579,495 B2
(45) Date of Patent: Aug. 25, 2009

(54) ACTIVE-RELEASING CYCLIC SILOXANES

(75) Inventors: Robert J. Perry, Niskayuna, NY (US); Mark D. Leatherman, Elmsford, NY (US); Shahid Murtuza, Albany, NY (US)

(73) Assignee: Momentive Performance Materials Inc., Albany, NY (US)

( * ) Notice: Subject to any disclaimer, the term of this patent is extended or adjusted under 35 U.S.C. 154(b) by 993 days.

(21) Appl. No.: 10/742,033

(22) Filed: Dec. 19, 2003

(65) Prior Publication Data
US 2005/0136021 A1 Jun. 23, 2005

(51) Int. Cl.
*C07F 7/18* (2006.01)
(52) U.S. Cl. .................. 556/406; 556/451; 556/464
(58) Field of Classification Search .............. 424/70.12, 424/70.121; 556/406, 451, 464
See application file for complete search history.

(56) References Cited

U.S. PATENT DOCUMENTS

| | | | |
|---|---|---|---|
| 3,215,719 A | 11/1965 | Allen et al. | |
| 3,271,305 A | 9/1966 | Allen et al. | |
| 4,445,641 A | 5/1984 | Baker et al. | |
| 4,500,725 A | 2/1985 | Yemoto et al. | |
| 4,524,018 A | 6/1985 | Yemoto et al. | |
| 4,908,208 A | 3/1990 | Lee | |
| 5,008,115 A | 4/1991 | Lee et al. | |
| 5,049,182 A | 9/1991 | Scher et al. | |
| 5,071,704 A | 12/1991 | Fischel-Ghodsian | |
| 5,130,171 A | 7/1992 | Prud'Homme et al. | |
| 5,139,864 A | 8/1992 | Lindauer | |
| 5,160,494 A | 11/1992 | Krzysik et al. | |
| 5,176,903 A | 1/1993 | Goldberg et al. | |
| 5,185,155 A | 2/1993 | Behan et al. | |
| 5,213,409 A | 5/1993 | Fisher | |
| 5,234,689 A | 8/1993 | Lindauer et al. | |
| 5,324,444 A | 6/1994 | Berry et al. | |
| 5,372,806 A | 12/1994 | Holloway | |
| 5,378,468 A | 1/1995 | Suffis et al. | |
| 5,387,411 A | 2/1995 | Abrutyn et al. | |
| 5,387,622 A | 2/1995 | Yamamoto | |
| 5,449,512 A | 9/1995 | Simmons | |
| 5,490,982 A | 2/1996 | Siclliano | |
| 5,500,223 A | 3/1996 | Behan et al. | |
| 5,525,555 A | 6/1996 | Zank | |
| 5,525,588 A | 6/1996 | Michetti | |
| 5,847,179 A | 12/1998 | LeGrow et al. | |
| 5,867,755 A | 2/1999 | Sato | |
| 6,042,792 A | 3/2000 | Shefer et al. | |
| 6,046,156 A | 4/2000 | Perry | |
| 6,054,547 A | 4/2000 | Perry et al. | |
| 6,063,365 A | 5/2000 | Shefer et al. | |
| 6,075,111 A | 6/2000 | Perry et al. | |
| 6,077,923 A | 6/2000 | Perry et al. | |
| 6,083,901 A | 7/2000 | Perry et al. | |
| 6,121,343 A | 9/2000 | Hongo et al. | |
| 6,143,309 A | 11/2000 | Legrow et al. | |
| 6,153,578 A | 11/2000 | Perry | |
| 6,200,949 B1 | 3/2001 | Reijmer et al. | |
| 6,228,380 B1 | 5/2001 | LeGrow et al. | |
| 6,262,287 B1 | 7/2001 | Anderson et al. | |
| 6,267,977 B1 | 7/2001 | LeGrow et al. | |
| 6,309,715 B1 | 10/2001 | Lindauer et al. | |
| 6,322,777 B1 | 11/2001 | Perry et al. | |
| 6,325,274 B2 | 12/2001 | Esumi et al. | |
| 6,325,859 B1 | 12/2001 | De Roos et al. | |
| 6,435,423 B2 | 8/2002 | Hurry et al. | |
| 6,624,136 B2 | 9/2003 | Guerin et al. | |

FOREIGN PATENT DOCUMENTS

| | | |
|---|---|---|
| EP | 106124 A2 | 9/1983 |
| EP | 106124 B1 | 9/1983 |
| EP | 273266 A2 | 12/1987 |
| EP | 273266 A3 | 12/1987 |
| EP | 0334490 A2 | 2/1989 |
| EP | 0334490 A3 | 2/1989 |
| EP | 0334490 B1 | 2/1989 |
| EP | 878497 A2 | 5/1998 |
| EP | 878497 A3 | 5/1998 |
| EP | 0 878 497 A | 11/1998 |
| EP | 1178107 A2 | 7/2000 |
| EP | 1178107 A3 | 7/2000 |
| EP | 1116515 A2 | 12/2000 |
| EP | 1116515 A3 | 12/2000 |
| EP | 1133929 A1 | 3/2001 |
| GB | 2041964 A | 1/1980 |
| GB | 2042890 A | 1/1980 |
| JP | 11047581 A | 2/1999 |
| JP | 2002020783 A | 1/2002 |
| WO | WO9628497 A1 | 9/1996 |
| WO | WO9815192 A1 | 4/1998 |
| WO | WO0016643 A1 | 3/2000 |
| WO | WO0016643 A5 | 3/2000 |
| WO | WO0064497 A1 | 11/2000 |
| WO | WO0173188 A1 | 10/2001 |
| WO | WO0179303 A1 | 10/2001 |
| WO | WO0206585 A1 | 1/2002 |
| WO | WO0241709 A1 | 5/2002 |
| WO | WO02076514 A2 | 10/2002 |
| WO | WO02076514 A3 | 10/2002 |
| WO | WO02083620 A1 | 10/2002 |
| WO | WO03032749 A1 | 4/2003 |

*Primary Examiner*—Elvis O Price
(74) *Attorney, Agent, or Firm*—Kenneth S. Wheelock

(57) ABSTRACT

Cyclic siloxanes that contain releasable active ingredients are described. The active ingredient can be an alcohol or enolizable carbonyl-containing compound such as a ketone, aldehyde, or ester. The product siloxanes are useful in a variety of personal and household care products where slow or controlled release of active ingredient is desired. A preferred embodiment utilizes substituents that when released as active ingredients are fragrant.

21 Claims, No Drawings

ACTIVE-RELEASING CYCLIC SILOXANES

CROSS-REFERENCE TO RELATED APPLICATIONS

Not Applicable

STATEMENT REGARDING FEDERALLY FUNDED RESEARCH

Not Applicable

FIELD OF THE INVENTION

The present invention relates to cyclic siloxanes suitable for use in a variety of applications including personal care formulations, household products, automotive, textiles and molding materials wherein the cyclic siloxane has been chemically modified to release an active ingredient upon hydrolysis. The present invention further relates to such molecules where the rate of active ingredient release is sufficiently slow so that products formulated with the modified cyclic siloxane exhibit desirable effects for long periods of time.

BACKGROUND OF THE INVENTION

The slow, sustained release of an active ingredient is a highly desirable trait in many personal care, textile, automotive, plastic, laundry and household products. A number of means have been proposed and implemented to achieve this goal. Among these means are dissolving or suspending fragrant compounds in personal care emulsions (U.S. Pat. No. 5,525,588; U.S. Pat. No. 5,525,555; U.S. Pat. No. 5,490,982; U.S. Pat. No. 5,372,806; EP 0334490; WO 0064497), encapsulation of a fragrant compound (U.S. Pat. No. 5,500,223; U.S. Pat. No. 5,324,444; U.S. Pat. No. 5,185,155; U.S. Pat. No. 5,176,903; U.S. Pat. No. 5,130,171; U.S. Pat. No. 6,325,859; U.S. Pat. No. 6,309,715; U.S. Pat. No. 6,325,274; U.S. Pat. No. 6,213,409; U.S. Pat. No. 6,200,949; U.S. Pat. No. 6,042,792; U.S. Pat. No. 5,867,755; U.S. Pat. No. 5,049,182; U.S. patent applications 20020187221, 20020009522, and 20010008635; EP 1116515, EP 1061124, EP 1133929; WO 0179303, WO 0173188, WO 9815192, WO 02076541), dissolving a fragrant compound into a hydrophobic phase such as a silicone (U.S. Pat. No. 5,449,512; U.S. Pat. No. 5,160,494; U.S. Pat. No. 5,234,689; WO 0241709), incorporation of a fragrant compound into crosslinked polymers (U.S. Pat. No. 6,435,423; U.S. Pat. No. 5,139,864; U.S. Pat. No. 6,379,689; U.S. Pat. No. 5,387,622; U.S. Pat. No. 5,387,411; WO 03032749; WO 02065858; JP 11047581), incorporation of fragrant compounds into permeable laminates (U.S. Pat. No. 6,500,444; U.S. Pat. No. 5,071,704; U.S. Pat. No. 5,008,115), incorporation of fragrant compounds into matrices that soften at body temperature (U.S. Pat. No. 4,908,208; EP 1178107; WO 0016643), incorporation of fragrant compounds into matrices that biodegrade (U.S. Pat. No. 6,121,343) or are bioactivated (U.S. Pat. No. 5,378,468), incorporation of fragrant compounds into rate controlling membranes (U.S. Pat. No. 6,063,365 and U.S. Pat. No. 4,445,641), derivatization of silanes with fragrant alcohols to form alkoxy silanes (U.S. Pat. No. 4,524,018 and U.S. Pat. No. 4,500,725), and derivatization of fragrances to form photosensitive molecules that release the fragrance upon exposure to light (WO 02083620; JP2002020783A). Derivatization of actives to give hydrolyzable organic (i.e., not containing silicon) molecules has also been well documented in the literature.

The marriage of silicon-containing molecules with active ingredients is of particular interest since many active ingredients are highly functional organics and suffer from incompatibility with the silicones that are found in personal and consumer care products, leading to syneresis and other phase separation phenomena. Derivatization of silanes with long-chain alcoholic skin care actives to give alkoxytrimethysilanes (U.S. Pat. No. 5,847,179) and derivatization of silanes with hydroxycarboxylic acid skin exfoliants to form (triorganosilyl)alkoxycarboxylates (U.S. Pat. No. 6,143,309; U.S. Pat. No. 6,228,380; U.S. Pat. No. 6,267,977) have been described. Direct displacement of an alkoxy leaving group on a silicon atom by a fragrant alcohol was reported by Allen, et al. to give fragrant silicon esters or linear silicate esters (U.S. Pat. No. 3,215,719 and U.S. Pat. No. 3,271,305). Several others also reported similar alkoxy displacement reaction to form linear fragrant siloxane polymers or copolymers (GB 2,041,964; GB 2,042,890; EP 273266). Reaction of an alcohol, aldehyde, ketone or lactone with a silyl hydride in the presence of a metal carboxylate salt and a reducing agent to form linear polymers and copolymers was also reported (WO 9628497). Other routes to fragrant silicones using silyl hydrides were disclosed by Anderson, et al. (EP 878497; JP 10330382; U.S. Pat. No. 6,262,287) and Perry, et al. (U.S. Pat. No. 6,046,156; U.S. Pat. No. 6,077,923; U.S. Pat. No. 6,153,578; U.S. Pat. No. 6,054,547; U.S. Pat. No. 6,075,111; U.S. Pat. No. 6,322,777; U.S. Pat. No. 6,083,901). In these processes, hydrosilylation chemistry was employed to join the active portion of the molecule to the silicone backbone.

SUMMARY OF THE INVENTION

The present invention provides for an active ingredient-releasing cyclic siloxane having formula I or II:

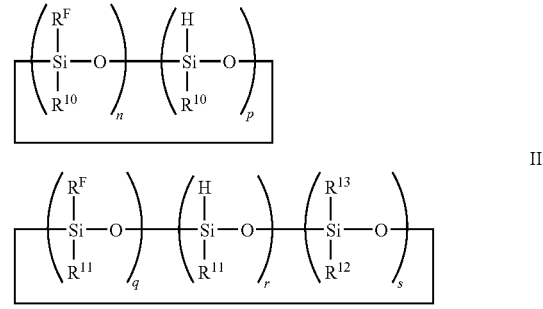

$R^{10}$, $R^{11}$, $R^{12}$, and $R^{13}$ are each independently selected from the group of monovalent $C_1$-$C_{24}$ hydrocarbon radicals. As used herein, the phrase monovalent hydrocarbon radical includes both aliphatic and aromatic monovalent hydrocarbon radicals that may also include heteroatoms such as oxygen, nitrogen, phosphorous, and sulfur as well as the halogens fluorine, chlorine, bromine, and iodine. The quantities n and q are each independently greater than or equal to 1, and the quantities p, r, and s are each independently equal to or greater than 0 with the proviso that n+p must be equal to or greater than 3 and that q+r+s must be equal to or greater than 3.

$R^F$ has the formula $(R^1O)_a(R^2O)_b(R^3O)_c(R^4)_d(R^5)_e SiR^U$ with $R^U$ defined as a $C_2$-$C_{40}$ monovalent unsaturated hydrocarbon radical (which when having undergone hydrosilylation becomes a $C_2$-$C_{40}$ divalent hydrocarbon radical), where $R^1$, $R^2$ and $R^3$ are independently selected or derived from group F or group G. Group F is defined as the group of alcohols consisting of $R^1OH$, $R^2OH$, and $R^3OH$, wherein $R^1OH$, $R^2OH$, and $R^3OH$ are alcoholic active ingredients, and group G is defined as the group of active ingredient esters, ketones, or aldehydes, each independently having the structure:

$$R^7—C(R^8)=C(O—)—R^9$$

with $R^4$ and $R^5$ each independently selected from the group consisting of monovalent hydrocarbon radicals having from one to forty carbon atoms and monovalent alkoxy radicals having from one to forty carbon atoms, $R^6$ a two to forty carbon atom monovalent unsaturated hydrocarbon radical containing a terminal olefinic or acetylenic moiety. The subscript a has a value ranging from 1 to 3 and the subscripts b, c, d, and e have values ranging from 0 to 2 subject to the limitation that a+b+c+d+e=3. $R^7$, $R^8$, and $R^9$ are each independently selected from the group consisting of hydrogen and monovalent hydrocarbon radicals having one to one hundred carbon atoms.

The present invention also provides for compositions that comprise an active ingredient releasing siloxane. Of particular use are cosmetic compositions that comprise an active ingredient releasing siloxane such as perfumes, skin creams, makeup, foundations and the like, as well as laundry agents such as detergent compositions, rinse additives, fabric softeners and the like.

DETAILED DESCRIPTION OF THE INVENTION

The compounds of the present invention introduce active ingredient moieties via hydrosilylation of an olefinic silane molecule. These resulting siloxane molecules are useful in a variety of consumer care compositions. The present invention is directed to new compositions of matter that are siloxanes that release an alcoholic or carbonyl-containing active ingredient upon hydrolysis, where the active ingredient can be illustrated by but not limited to adhesion promoters, adhesives, anti-aging agents, antioxidants, antiperspirants, antistatic agents, biocides, bittering agents, bleaching agents, brighteners, colorants, conditioners, defoamers, detergents, disinfectants, dispersing agents, fillers, foaming agents, foam stabilizers, fragrances, humectants, hydrotropes, insect repellants, liquid crystals, moisturizers, odor absorbers, opacifying agents, oral care additives, pharmaceuticals, preservatives, rheology modifiers, screening agents, sequestering or chelating agents, solubilizers, solvents, sunscreens, surfactants, suspending agents, tanning agents, thickeners, vitamins or other nutrients, or whitening agents.

The olefinic silanes utilized by the present invention are described by the formula:

$$(R^1O)_a(R^2O)_b(R^3O)_c(R^4)_d(R^5)_eSiR^6$$

where $R^1O$, $R^2O$ and $R^3O$ are independently derived from group F or group G. Group F is the group of alcohols consisting of $R^1OH$, $R^2OH$, and $R^3OH$, wherein $R^1OH$, $R^2OH$, and $R^3OH$ are alcoholic active ingredients, where $R^1$, $R^2$ and $R^3$ are independently monovalent hydrocarbon radicals having from four to one hundred carbon atoms, preferably five to one hundred carbon atoms, more preferably six to one hundred carbon atoms and most preferably seven to one hundred carbon atoms that may also contain hetero-atoms such as oxygen, sulfur, nitrogen, phosphorus and the halogens fluorine, chlorine, bromine and iodine. Group G is the group of carbonyl-containing actives, or carbonyl active ingredients, each independently having the structure:

$$R^7—CH(R^8)(C=O)—R^9$$

wherein the carbonyl-containing active is capable of exhibiting the enol form of the carbonyl moiety under reaction conditions as shown:

$$R^7—CH(R^8)(C=O)—R^9 \rightarrow R^7—C(R^8)=C(OH)—R^9$$

and which will react through the enol hydroxyl group to form a carbon-oxygen-silicon linkage (i.e. $R^7—C(R^8)=C(O—)—R^9$) where the hyphen after the oxygen in the formula indicates the species is a monovalent radical and independently describes $R^1$, $R^2$ and $R^3$), with $R^4$ and $R^5$ selected from the group consisting of monovalent hydrocarbon radicals having from one to forty carbon atoms and monovalent alkoxy radicals having from one to forty carbon atoms, $R^6$ a $C_2$-$C_{40}$ monovalent unsaturated hydrocarbon radical containing a reactive olefinic or acetylenic moiety, which is preferably a terminal olefin or acetylene, where the subscript a has a value ranging from 1 to 3 and the subscripts b, c, d, and e have values ranging from 0 to 2 subject to the limitation that a+b+c+d+e=3; $R^7$, $R^8$, and $R^9$ are each independently selected from the group consisting of hydrogen and monovalent hydrocarbon radicals having from one to one hundred carbon atoms. It should be noted that the structure:

$$R^7—C(R^8)=C(O—)—R^9$$

is a conjugate structure that corresponds to the enol structure:

$$R^7—C(R^8)=C(OH)—R^9$$

but missing the hydroxyl hydrogen. In the structure:

$$R^7—C(R^8)=C(O—)—R^9$$

the hyphen after the oxygen atom indicates a univalent bonding site wherein the structure is a monovalent radical. As used herein, the phrase from one to one hundred carbon atoms is chosen wherein the class of available carbonyl-containing actives is subtended by the formula $R^7—CH(R^8)(C=O)—R^9$. As used herein, the phrase monovalent hydrocarbon radical includes both aliphatic and aromatic monovalent hydrocarbon radicals that may also include heteroatoms such as oxygen, nitrogen, phosphorous, sulfur and the halogens fluorine, chlorine, bromine and iodine.

The following synthetic examples are intended to illustrate the general synthetic reactions schemes that a person having ordinary skill in the art of silicone chemistry would typically employ in order to prepare the olefinic silanes used by the present invention. These reaction schemes are thus illustrative only and do not represent the only synthetic pathways that may be utilized.

When the starting material is an alcoholic active ingredient such as phenethanol, olefinic halosilanes or olefinic silicon alkoxides may be employed as starting materials to produce the active ingredient releasing siloxanes of the present invention via active-bearing olefinic silanes (reaction schemes I-III).

Reaction scheme I:

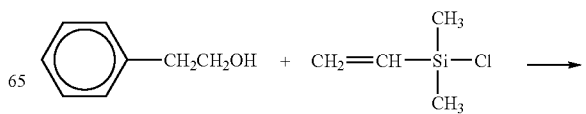

-continued

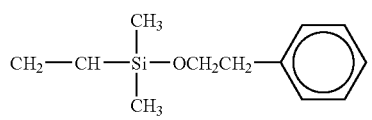

Reaction scheme V:

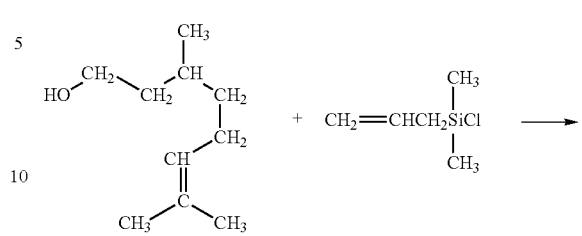

Reaction scheme II:

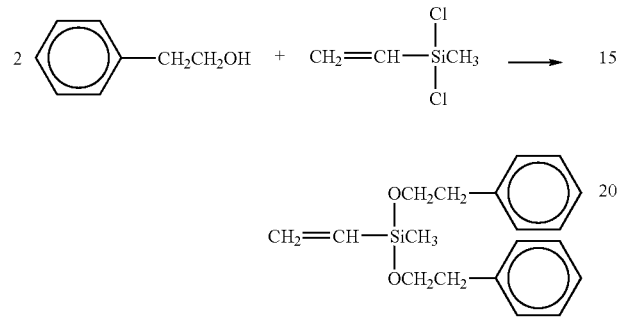

Reaction scheme III:

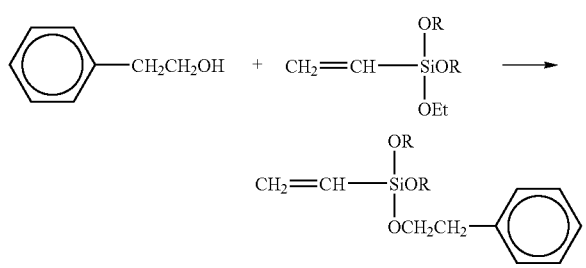

where the R groups for reaction III may be Et ($C_2H_5$—) or —$CH_2CH_2C_6H_5$. Similarly, 3-methyl-5-(2,2,3,-trimethyl-3-cyclopenten-1-yl)-4-penten-2-ol will react with chloromethylvinylsilane in a similar fashion (reaction scheme IV):

Reaction scheme IV:

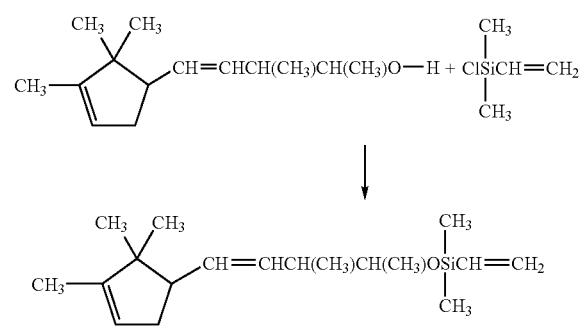

as will allyldimethylchlorosilane react with citronellol in a similar, reaction scheme V:

Representative alcohols that are precursors of the active-containing silanes or siloxanes of the present invention may be illustrated by but not limited to acetovanillone, allyl amylglycolate, allyl isoamylglycolate, α-amylcinammyl alcohol, anisyl alcohol, benzoin, benzyl alcohol, benzyl salicylate, 1-butanol, butylated hydroxytoluene, butyl lactate, 2-t-butyl-5-methylphenol, 2-t-butyl-6-methylphenol, carvacrol, carveol, 4-carvomenthenol, cedrol, cetyl alcohol, cinnamic alcohol, citronellol, o-cresol, m-cresol, p-cresol, crotyl alcohol, decahydro-2-naphthol, 1-decanol, 1-decen-3-ol, 9-decen-1-ol, diethyl malate, diethyl tartrate, dihydrocarveol, dihydromyrcenol, 2,6-diisopropylphenol, dimethicone copolyol, 2,6-dimethoxyphenol, 1,1-dimethoxy-3,7-dimethyloctan-7-ol, 2,6-dimethyl-4-heptanol, 2,6-dimethylheptan-2-ol, 6,8-dimethyl-2-nonanol, 3,7-dimethyl-2,6-octadien-1-ol, 3,7-dimethyl-1,6-octadien-3-ol, 3,7-dimethyl-1-octanol, 3,7-dimethyl-3-octanol, 3,7-dimethyl-6-octen-1-ol, 3,7-dimethyl-7-octen-1-ol, dimetol, 2-ethylfenchol, 4-ethylguaiacol, 2-ethyl-1-hexanol, ethyl 2-hydroxybenzoate, ethyl 3-hydroxybutyrate, 3-ethyl-2-hydroxy-2-cyclopenten-1-one, ethyl 2-hydroxycaproate, ethyl 3-hydroxyhexanoate, ethyl lactate, ethyl maltol, p-ethylphenol, ethyl salicylate, eugenol, farnesol, fenchyl alcohol, geraniol, glucose petaacetate, glycerol, glyceryl monostearate, guaiacol, 1-heptanol, 2-heptanol, 3-heptanol, cis-4-heptenol, cis-3-heptenol, n-hexanol, 2-hexanol, 3-hexanol, cis-2-hexenol, cis-3-hexenol, trans-3-hexenol, 4-hexenol, cis-3-hexenyl hydrocinnamyl alcohol, 2-hydroxybenzoate, 2-hydroxyacetophenone, 4-hydroxybenzyl alcohol, 3-hydroxy-2-butanone, hydroxycitronellal, 4-(4-hydroxy-3-methoxyphenyl)-2-butanone, 2-hydroxy-3-methyl-2-cyclopenten-1-one, 4-(p-hydroxyphenyl)-2-butanone, 2-hydroxy-3,5,5-trimethyl-2-cyclohexenone, δ-isoascorbic acid, isoborneol, isoeugenol, isophytol, isopropyl alcohol, p-isopropylbenzyl alcohol, 4-isopropylcylcohexanol, 3-isopropylphenol, 4-isopropylphenol, 2-isopropylphenol, isopulegol, lauryl alcohol, linalool, maltol, menthol, 4-methoxybenzyl alcohol, 2-methoxy-4-methylphenol, 2-methoxy-4-propylphenol, 2-methoxy-4-vinylphenol, α-methylbenzyl alcohol, 2-methylbutanol, 3-methyl-2-butanol, 3-methyl-2-buten-1-ol, 2-methyl-3-buten-2-ol, methyl 2,4-dihydroxy-3,6-dimethylbenzoate, 4-methyl-2,6-dimethoxyphenol, methyl N-3,7-dimethyl-7-hydroxyoctylideneanthranilate, methyl 3-hydroxyhexanoate, 6-methyl-5-hepten-2-ol, 2-methylpentanol, 3-methyl-3-pentanol, 2-methyl-4-phenylbutan-2-ol, 2-methyl-3-phenylpropan-2-ol, methyl salicylate, 3-methyl-5-(2,2,3,-trimethyl-3-cyclopenten-1-yl)-4-penten-2-ol, 2-methyl-2-vinyl-5-(1-hydroxy-1-methyl ethyl)-3,4-dihydrofuran, myrtenol, neohesperidin dihydrochalcone, neomenthol, nerol, nerolidol, trans-2-cis-6-nonadienol, 1,3-nonanediol acetate, nonadyl, 2-nonanol, cis-6-nonen-1-ol, trans-2-nonen-1-ol, nonyl alcohol, 1-octanol, 2-octanol, 3-octanol, cis-3-octen-1-ol, cis-2-octen-1-ol, trans-2-octen-1-ol, cis-6-octen-1-ol, cis-octen-1-ol, 1-octen-3-ol, oleyl alcohol, patchouli alcohol, 3-pentanol, n-pentanol, 2-pentanol, 1-penten-1-ol, cis-2-penten-1-ol, perillyl alcohol, 2-phenoxyethanol arabinogalactan, β-phenethyl alcohol, phenethyl salicylate, phenol, phenylacetaldehyde glyceryl acetal, 3-phenyl-1-pentanol, 5-phenyl-1-pentanol, 1-phenyl-1-pentanol, 1-phenyl-2-pentanol, 1-phenyl-3-methyl-1-pentanol, phytol, pinacol, polyalkylene glycols, polysorbate 20, polysorbate 60, polysorbate 80, prenol, n-propanol, propenyl guaethol, propylene glycol, 2-propylphenol, 4-propylphenol, resorcinol, retinol, salicylaldehyde, sorbitan monostearate, sorbitol, stearyl alcohol, syringealdehyde, α-terpineol, tetrahydrogeraniol, tetrahydrolinalool, tetrahydromyrcenol, thymol, triethyl citrate, 1,2,6-trihydroxyhexane, p-α,α-trimethylbenzyl alcohol, 2-(5,5,6-trimethylbicyclo[2.2.1]hept-2-ylcyclohexanol, 5-(2,2,3-trimethyl-3-cyclopentenyl)-3-methylpentan-2-ol, 3,7,-11-trimethyl-2,6,10-dodecatrien-1-ol, 3,7,11-trimethyl-1,6,10-dodecatrien-3-ol, 3,5,5-trimethyl-1-hexanol, 10-undecen-1-ol, undecyl alcohol, vanillin, o-vanillin, vanillyl butyl ether, 4-vinylphenol, 2,5-xylenol, 2,6-xylenol, 3,5-xylenol, 2,4-xylenol, and xylose.

When the starting material is a carbonyl-containing active ingredient such as 2-methyl-3-(4-t-butylphenyl)propanal, olefinic halosilanes or olefinic silicon alkoxides may be employed as starting materials to produce the active-releasing siloxanes of the present invention via active ingredient bearing olefinic silanes.

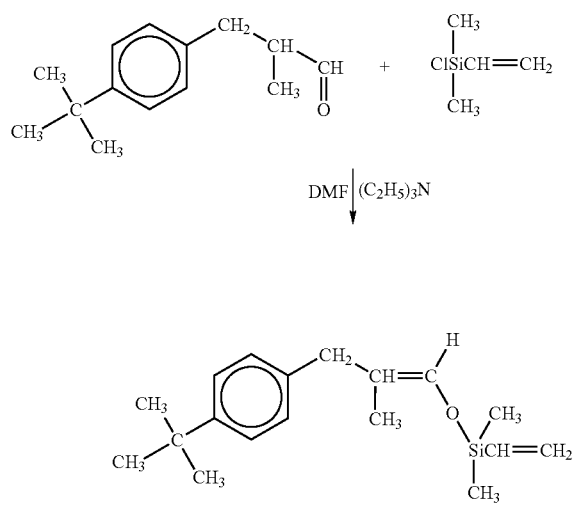

Note that DMF is dimethylformamide. This reaction scheme may also be used to prepare the 3-methyl-3-(3-(1-methylethylphenyl))propanal derivative:

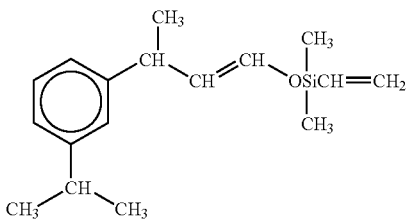

The reaction of carbonyl-containing species, e.g. esters, ketones and aldehydes, requires the establishment of the keto enol tautomeric equilibrium.

Tautomerism is the chemical phenomenon of the establishment of an equilibrium between two or more structurally distinct compounds. In nearly all cases, the difference between one tautomeric form of the equilibrium compounds and the other is the isomeric placement of a hydrogen atom. A prevalent form of tautomerism is the tautomeric equilibrium established between a carbonyl compound (i.e. one containing a carbonyl group) and having a hydrogen atom alpha to the carbonyl group, i.e. an α hydrogen:

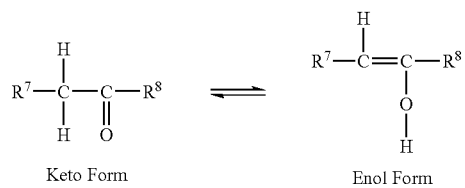

Keto Form      Enol Form

Generally the equilibrium constant favors the keto form and the equilibrium lies well to the left. The extent of enolization is greatly affected by solvent, concentration and temperature. When a strong base is present, both the enol and the keto form can lose a hydrogen ion (a proton), forming an enolate anion:

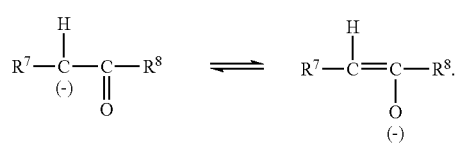

Since both of these structures differ only in the placement of electrons, these are canonical forms of the same ion rather than tautomeric isomers. Because oxygen is more electronegative than carbon, the predominate canonical form is the one where the ionic charge is more localized on the oxygen atom. While the tautomeric equilibrium between enols and ketones or aldehydes is not normally a preparative reaction, the equilibrium must occur since ketones and aldehydes often react through their enol forms as they do instantly in the preparation of the compounds of the present invention. This keto-enol tautomeric equilibrium is also established for esters or organic acids, i.e. in the structures above when $R^8$ includes an oxygen bound to an appropriate R group, e.g. OR', the compound is an organic ester. For a more detailed explanation of this chemistry see J. March "Advanced Organic Chemistry," John Wiley & Sons, New York (1985), pp. 66-68 and 527-529 and references therein.

Fragrant molecules, alcohols, ketones and aldehydes, may be reacted as the alcohol or enol tautomer to produce silicone or siloxanes bearing fragrant moieties. The reaction involves reaction of the alcoholic or enolic form of the molecule with hydrogen, hydroxyl or halogen directly bonded to a silicon atom to form the fragrant derivative. The reaction involves formation of the conjugate base related to the alcohol or enol tautomeric form of the molecule:

R″OH dissociates to $H^+$ and $R″O^-$ (conjugate base), n=1, 2 or 3 (thus $R^1$ etc. as previously defined);

where R″OH is a fragrant alcohol or the enol tautomeric form of a fragrant ketone or aldehyde. Aldehydes and ketones react with alcohol(s) R'OH to form hemiacetals (derived from aldehydes) or hemiketals (derived from ketones): RCH(O)+ R'OH→RCH(OH)(OR') hemiacetal, which has a conjugate base obtained by removing the hydroxyl hydrogen: RCH(O$^-$)(OR') and RC(O)R″+R'OH→RC(OH)(R'O)R″ which has a conjugate base likewise obtained by removing the hydroxyl hydrogen: RC(O$^-$)(R'O)R″. As used herein the R″ are fragrant moieties, i.e. monovalent radicals, either as a neutrally charged monovalent radical (R″ or R″O) or as a charged monovalent radical, derived from the conjugate bases of fragrant molecules, e.g. $R''^+ + O^{-2} → R''O^-$.

Representative carbonyl-containing active ingredients that are precursors of the active-containing silanes of the present invention may be illustrated by but not limited to 4-acetoxy-3-pentyl-tetrahydropyran, allyl cinnamate, allyl 2-ethylbutyrate, allyl cyclohexanepropionate, allyl heptanoate, allyl hexanoate, allyl isovalerate, allyl nonanoate, allyl octanoate, allyl phenoxyacetate, allyl phenylacetate, allyl propionate, α-amylcinnamyl acetate, amyl octanoate, anisyl acetate, anisylphenyl acetate, benzyl acetate, benzyl acetoacetate, benzyl butyrate, benzyl cinnamate, benzyl isobutyrate, benzyl isovalerate, benzyl phenylacetate, benzyl propionate, bornyl acetate, bornyl isovalerate, bornyl valerate, butyl acetate, butyl butyrate, butyl butyryllactate, 4-t-butylcyclohexyl acetate, butyl heptanoate, butyl hexanoate, butyl isobutyrate, butyl isovalerate, butyl laurate, butyl propionate, butyl stearate, 3-butylidenephthalide, butyl 2-methylbutyrate, butyl 10-undeceneoate, γ-butyrolactone, carvyl acetate, carvyl propionate, caryophyllene acetate, cedryl acetate, trans-cinnamyl acetate, trans-cinnamyl butyrate, cinnamyl cinnamate, cinnamyl isobutyrate, citronellyl acetate, citronellyl butyrate, citronellyl isobutyrate, citronellyl propionate, citronellyl valerate, cyclohexaneethyl acetate, cyclohexyl acetate, cyclohexyl butyrate, cyclohexyl isovalerate, cyclohexyl propionate, δ-decalactone, ε-decalactone, γ-decalactone, 4-decanolide, decyl acetate, decyl butyrate, decyl propionate, diethyl malonate, diethyl sebacate, diethyl succinate, dihydrocarvyl acetate, dihydrocoumarin, dihydromyrcenyl acetate, dihydro-nor-dicyclopentadienyl acetate, dihydroterpinyl acetate, 3,7-dimethyl-1,6-octadien-3-yl acetate, 3,7-dimethyl-1,6-octadien-3-yl propionate, 3,7-dimethyloctan-3-yl acetate, α,α-dimethylphenethyl acetate, α,α-dimethylphenethyl butyrate, 6,10-dimethyl-5,9-undecadien-2-yl acetate, δ-dodecalactone, ε-dodecalactone, γ-dodecalactone, ethyl acetate, ethyl acetoacetate, ethyl 6-acetoxyhexanoate, ethyl 2-acetyl-3-phenylpropionate, ethyl benzoylacetate, 2-ethylbutyl acetate, ethyl butyrate, ethyl cinnamate, ethyl cyclohexanepropionate, ethyl decanoate, ethylene brassylate, ethyl 2-ethyl-6,6-dimethyl-2-cyclohexenecarboxylate, ethyl 2,3-epoxybutyrate, ethyl 2-methyl-4-penteneoate, ethyl heptanoate, ethyl hexanoate, ethyl trans-3-hexenoate, 2-ethylhexyl acetate, ethyl isobutyrate, ethyl isovalerate, ethyl laurate, ethyl 2-mercaptopropionate, ethyl 3-mercaptopropionate, ethyl 2-methylbutyrate, ethyl 2-methylpentanoate, ethyl (methylthio)acetate, methyl (methylthio) acetate, methyl 2-(methylthio) propionate, ethyl myristate, ethyl nonanoate, ethyl octanoate, ethyl palmitate, ethyl phenylacetate, ethyl 3-phenylpropionate, ethyl 3-phenyl-2,3-epoxybutyrate, ethyl 3-phenylpropionate, ethyl propionate, ethyl stearate, ethyl 2,3,6,6-tetramethyl-2-cyclohexencarboxylate, ethyl (p-tolyloxy)acetate, ethyl undecanoate, ethyl valerate, eugenyl acetate, fenchyl acetate, geranyl acetate, geranyl butyrate, geranyl phenylacetate, geranyl propionate, guaiacyl phenylacetate, guaicwood acetate, γ-heptalactone, heptyl acetate, heptyl butyrate, heptyl isobutyrate, ω-6-hexadecenlactone, δ-hexylactone, γ-hexylactone, 3-hexenyl acetate, cis-3-hexenyl 2-methylbutanoate, cis-3-hexenyl cis-3-hexenoate, cis-3-hexenyl phenylacetate, trans-2-hexenyl acetate, hexyl acetate, hexyl butyrate, hexyl hexanoate, hexyl isobutyrate, hexyl propionate, hexyl 2-methybutanoate, hexyl 3-methylbutanoate, hexyl phenylacetate, isoamyl acetate, isoamyl acetoacetate, isoamyl butyrate, isoamyl cinnamate, isoamyl hexanoate, isoamyl isobutyrate, isoamyl isovalerate, isoamyl laurate, isoamyl nonanoate, isoamyl octanoate, isoamyl phenylacetate, isoamyl propionate, isobornyl acetate, isobornyl propionate, isobutyl acetate, isobutyl butyrate, isobutyl cinnamate, isobutyl hexanoate, isobutyl isobutyrate, isobutyl 2methylbutyrate, isobutyl propionate, isoeugenyl acetate, isopropyl cinnamate, isobutyl phenylacetate, isopropyl acetate, isopropyl butyrate, isopropyl isobutyrate, isopropyl myristate, isopropyl palmitate, isopropyl phenylacetate, lauryl acetate, linalyl acetate, linalyl butyrate, linalyl isovalerate, menthalactone, menthyl acetate, menthyl cyclohexanecarboxylate, menthyl isovalerate, 4-methoxybenzyl acetate, 4-methoxybenzyl propionate, 2-methoxyphenyl acetate, 2-methoxy-4-(1-propenyl)phenyl acetate, methyl acetate, α-methylbenzyl acetate, α-methylbenzyl butyrate, α-methylbenzyl propionate, 2-methylbutyl acetate, 2-methylbutyl butyrate, 2-methylbutyl isovalerate, 3-methylbutyl 2-methylbutanoate, 2-methylbutyl 2-methylbutanoate, methyl p-t-butylphenylacetate, methyl butyrate, methyl cinnamate, methyl decanoate, methyl heptanoate, methyl hexanoate, methyl isobutyrate, methyl isovalerate, methyl laurate, methyl N-2-methyl-3-(4-t-butylphenylpropylidene) anthranilate, methyl myristate, methyl nonanoate, methyl octanoate, methyl palmitate, 4-(4-methyl-3-pentenyl)-3-cyclohexenylmethyl acetate, methyl 2-methylbutyrate, 2-methyl-6-methylen-7-octen-2-yl acetate, methyl 4-methylvalerate, methyl 2-methylpentanoate, methyl phenoxyacetate, 4-methylphenyl phenylacetate, 2-methyl-3-phenylpropan-2-yl acetate, methyl 3-phenylpropionate, methyl propionate, 2-methylpropyl phenylacetate, methyl phenylacetate, 2-methyl-3-phenylpropan-2-yl acetate, methyl stearate, methyl (p-tolyloxy)acetate, methyl 9-undecenoate, methyl valerate, myrtenyl acetate, neryl acetate, neryl butyrate, neryl isobutyrate, δ-nonalactone, γ-nonalactone, 1,3-nonanediol diacetate, nonyl acetate, nopyl acetate, octahydrocoumarin, γ-octalactone, 1-octen-3-yl acetate, 1-octen-3-yl butyrate, octyl acetate, actyl butyrate, octyl isobutyrate, octyl isovalerate, octyl octanoate, octyl propionate, oxacycloheptadec-10-en-2-one, ω-pentadecalactone, pentyl acetate, pentyl butyrate, pentyl hexanoate, pentyl octanoate, phenethyl acetate, phenethyl butyrate, phenethyl cinnamate, phenethyl hexanoate, phenethyl isobutyrate, phenethyl isovalerate, phenethyl 2-methylbutyrate, phenethyl 2-methylbutyrate, phenethyl 2-methylpropionate, phenethyl octanoate, phenethyl phenylacetate, phenethyl propionate, phenoxyethyl propionate, 2-phenoxyethyl 2-methylpropionate, 3-phenyl-2-propenyl propionate, 3-phenylpropyl acetate, 2-phenylpropyl butyrate, 2-phenylpropyl isobutyrate, 2-phenylpropyl isovalerate, piperonyl acetate, piperonyl isobutyrate, prenyl acetate, propyl acetate, propyl butyrate, propyl heptanoate, propyl hexanoate, 3-propylidenephthalide, propyl isobutyrate, propyl propionate, propyl phenylacetate, sucrose octaacetate, terpinyl acetate, terpinyl butyrate, terpinyl isobutyrate, terpinyl propionate, tetrahydrofurfuryl acetate, tetrahydrofurfuryl butyrate, tetrahydrofurfuryl propionate, tetrahydrolinalyl acetate, 2,6,6,8-tetramethyl-tricyclo[5.3.1.0(1.5)]udecan-8-yl acetate, p-tolyl acetate, p-tolyl isobutyrate, p-tolyl phenylacetate, triacetin, tributyl acetylcitrate, tributyrin, tripropionin, 3,5,5-trimethylhexyl acetate, δ-undecalactone, γ-undecalactone, γ-valerolactone, vanillin acetate, vanillyl isobutyrate, 1-vinyl-2-(1-methylpropyl)cyclohexyl acetate, whiskey lactone, butyraldehyde, citronellal, decanal, cis-4-decenal, trans-4-decenal, 2,4-dimethyl-3-cyclohexen-1-carbaldehyde, 2,6-dimethyl-5-heptenal, 3,7-dimethyloctanal, 2-ethylbutyraldehyde, glutaric dialdehyde, heptanal, cis-4-heptenal, hexanal, hydrocinnamaldehyde, isobutyraldehyde, 3-(p-isopropylphenyl)-propionaldehyde, isovaleraldehyde, lauric aldehyde, 2-methylbutyraldehyde, 2-methyl-3-(p-isopropylphenyl)propionaldehyde, 2-methylpentanal, 4-(4-methyl-3-pentenyl)-3-cyclohexen-1-carbaldehyde, 4-methylphenylacetaldehyde, 3-(methylthio)butanal, 2-methyl-4-(2,6,6-trimethyl-2-cyclohexen-1-yl)butanal, 2-methylundecanal, nonanal, cis-6-nonenal, octanal, phenylacetaldehyde, 2-phenylpropionaldehyde, 3-phenylpropionaldehyde, propionaldehyde, p-tolylacetaldehyde, tridecanal, 2,4,6-trimethyl-3-cyclohexen-1-carbaldehyde, 2,6,10-trimethyl-9-undecanal, 7-undecenal, 8-undecenal, 9-undecenal, 10-undecenal, valeraldehyde, acetanisole, 1'-acetonaphthone, 2'-acetonaphthone, acetone, acetophenone, 2-acetoxy-2,5-dimethyl-3(2H)furanone, 2-acetylcyclopentanone, 4-acetyl-1,1-dimethyl-6-t-butylindan, 7-acetyl-1,1,3,4,4,6-hexamethylindan, 2-acetyl-2-thizoline, 6-acetyl-1,1,2,4,4,7-hexamethyl tetralin, allyl α-ionone, benzylideneacetone, 2,3-butanedione, 2-sec-butylcyclohexanone, 5-t-butyl-3,5-dinitro-2,6-dimethylacetophenone, butyrophenone, camphor, 2-decanone, 3-decanone, 3-decen-2-one, dihydrocarvone, dihydro-β-ionone, dihydrojasmone, 4,5-dihydro-3(2H)-thiophenone, 2',4'-dimethylacetophenone, 3,4-dimethyl-1,2-cyclopentadione, 3,5-dimethyl-1,2-cyclopentadione, 2,6-dimethyl-4-heptanone, 1,3-diphenyl-2-propanone, 4-(1-ethoxyvinyl)-3,3,5,5-tetramethylcyclohexanone, p-ethylacetophenone, ethyl vinyl ketone, geranylacetone, 2,3-heptanedione, 2-heptanone, 3-heptanone, 4-heptanone, 3,4-hexanedione, 3-hexanone, 4-hexen-3-one, 2-hexylidene cyclopentanone, α-ionone, β-ionone, 4-isobutyl-2,6-dimethyl-3,5-dinitroacetophenone, isophorone, 6-isopropyldecahydro-2-naphthone, cis-jasmone, livescone, 4-methoxyacetophenone, 4-(p-methoxyphenyl)-2-butanone, 4'-methylacetophenone, 3-methyl-1,2-cyclohexanedione, 3-methyl-2-cyclohexen-1-one, 2-(2-(4-methyl-3-cylcohexen-1-yl)propyl)-cyclopentanone, 3-methyl-2-cyclopenten-1-one, methyl dihydrojasmonate, methyl ethyl ketone, 2-methyl-3-heptanone, 5-methyl-2-hepten-4-one, 6-methyl-5-hepten-2-one, 5-methyl-α-ionone, 1-(2-methyl-5-isopropyl-2-cyclohexenyl)-1-propanone, 4-methyl-2-pentanone, 3-methyl-2-(2-pentenyl)-2-cyclopenten-1-one, 4-methyl-1-phenyl-2-pentanone, 2-methyltetrahydrofuran-3-one, 2-methyltetrahydrothiophen-3-one, 2-nonanone, 3-nonanone, 2-octanone, 3-octanone, 1-octen-3-one, 3-octen-2-one, 4-oxoisophorone, 2-pentadecanone, 2,3-pentanedione, 2-pentanone, 3-pentanone, 3-penten-2-one, 1-phenyl-1,2propandione, propiophenone, pulegone, 2-tridecanone, 2,2,6-trimethylcyclohexanone, 4-(2,6,6-trimethyl-2-cylcohexen-1-yl)-3-methyl-3-buten-2-one, 2-undecanone, and 6-undecanone.

The active ingredient releasing siloxanes of the present invention are prepared from an organohydrogen siloxane via conventional hydrosilylation using the active-bearing olefinic silane as the alkenyl source, an example of this reaction being:

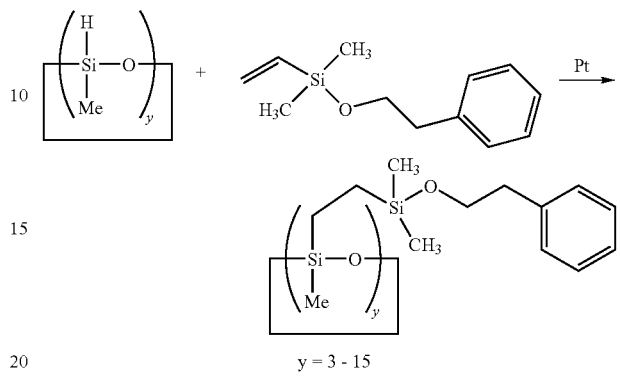

y = 3 - 15

In this specific instance, the siloxane species is actually a mixture of cyclic siloxanes with y ranging from 3-15.

Thus an organohydrogensiloxane having formula III or IV:

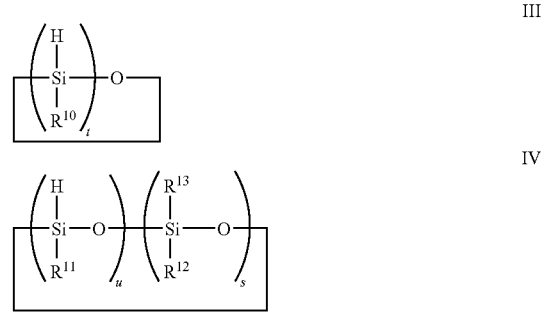

where $R^{10}$, $R^{11}$, $R^{12}$, and $R^{13}$ are each independently selected from the group of monovalent $C_1$-$C_{24}$ hydrocarbon radicals. The quantity t is greater than or equal to 3, the quantity u is greater than or equal to 1, and the quantity s is greater than or equal to 0, with the proviso that u+s must be equal to or greater than 3.

The organohydrogensiloxane is reacted under hydrosilylation conditions to produce an active-releasing siloxane having formula I or II:

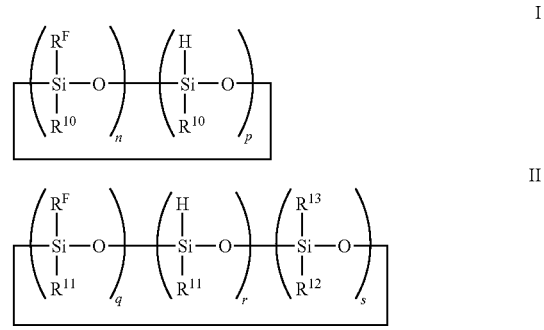

where the components and subscripts satisfy the previous definitions and requirements and $R^F$ has the formula $(R^1O)_a(R^2O)_b(R^3O)_c(R^4)_d(R^5)_eSiR^U$ with $R^U$ a $C_2$-$C_{40}$ divalent hydrocarbon radical where the subscripts and components are as previously defined. This siloxane undergoes a slow hydrolysis under most conditions of use whereby the siloxane releases an alcoholic or carbonyl-containing active ingredient upon hydrolysis. This imparts a desirable effect to many different useful compositions such as cosmetics and household products.

The hydrosilylation reaction is conventionally carried out in the presence of a hydrosilylation catalyst selected from the group of ruthenium, osmium, rhodium, iridium, palladium and platinum hydrosilylation catalysts. Exemplary of such catalysts are those described in U.S. Pat. Nos. 2,823,218; 3,159,601; 3,159,662; and 3,775,452.

The compositions of the present invention further provide that the active ingredient releasing siloxane have one or more substituents $R^1$, $R^2$, or $R^3$ where each substituent is independently selected whereby an alcoholic or carbonyl-containing active ingredient resulting from hydrolysis of said siloxane is selected from the group of alcohols consisting of acetovanillone, allyl amylglycolate, allyl isoamylglycolate, α-amylcinnammyl alcohol, anisyl alcohol, benzoin, benzyl alcohol, benzyl salicylate, 1-butanol, butylated hydroxytoluene, butyl lactate, 2-t-butyl-5-methylphenol, 2-t-butyl-6-methylphenol, carvacrol, carveol, 4-carvomenthenol, cedrol, cetyl alcohol, cinnamic alcohol, citronellol, o-cresol, m-cresol, p-cresol, crotyl alcohol, decahydro-2-naphthol, 1-decanol, 1-decen-3-ol, 9-decen-1-ol, diethyl malate, diethyl tartrate, dihydrocarveol, dihydromyrcenol, 2,6-diisopropylphenol, dimethicone copolyol, 2,6-dimethoxyphenol, 1,1-dimethoxy-3,7-dimethyloctan-7-ol, 2,6-dimethyl-4-heptanol, 2,6-dimethylheptan-2-ol, 6,8-dimethyl-2-nonanol, 3,7-dimethyl-2,6-octadien-1-ol, 3,7-dimethyl-1,6-octadien-3-ol, 3,7-dimethyl-1-octanol, 3,7-dimethyl-3-octanol, 3,7-dimethyl-6-octen-1-ol, 3,7-dimethyl-7-octen-1-ol, dimetol, 2-ethylfenchol, 4-ethylguaiacol, 2-ethyl-1-hexanol, ethyl 2-hydroxybenzoate, ethyl 3-hydroxybutyrate, 3-ethyl-2-hydroxy-2-cyclopenten-1-one, ethyl 2-hydroxycaproate, ethyl 3-hydroxyhexanoate, ethyl lactate, ethyl maltol, p-ethylphenol, ethyl salicylate, eugenol, farnesol, fenchyl alcohol, geraniol, glucose petaacetate, glycerol, glyceryl monostearate, guaiacol, 1-heptanol, 2-heptanol, 3-heptanol, cis-4-heptenol, cis-3-heptenol, n-hexanol, 2-hexanol, 3-hexanol, cis-2-hexenol, cis-3-hexenol, trans-3-hexenol, 4-hexenol, cis-3-hexenyl hydrocinnamyl alcohol, 2-hydroxybenzoate, 2-hydroxyacetophenone, 4-hydroxybenzyl alcohol, 3-hydroxy-2-butanone, hydroxycitronellal, 4-(4-hydroxy-3-methoxyphenyl)-2-butanone, 2-hydroxy-3-methyl-2-cyclopenten-1-one, 4-(p-hydroxyphenyl)-2-butanone, 2-hydroxy-3,5,5-trimethyl-2-cyclohexenone, 6-isoascorbic acid, isoborneol, isoeugenol, isophytol, isopropyl alcohol, p-isopropylbenzyl alcohol, 4-isopropylcylcohexanol, 3-isopropylphenol, 4-isopropylphenol, 2isopropylphenol, isopulegol, lauryl alcohol, linalool, maltol, menthol, 4-methoxybenzyl alcohol, 2-methoxy-4-methylphenol, 2-methoxy-4-propylphenol, 2-methoxy-4-vinylphenol, α-methylbenzyl alcohol, 2-methylbutanol, 3-methyl-2-butanol, 3-methyl-2-buten-1-ol, 2-methyl-3-buten-2-ol, methyl 2,4-dihydroxy-3,6-dimethylbenzoate, 4-methyl-2,6-dimethoxyphenol, methyl N-3,7-dimethyl-7-hydroxyoctylideneanthranilate, methyl 3-hydroxyhexanoate, 6-methyl-5-hepten-2-ol, 2-methylpentanol, 3-methyl-3-pentanol, 4-methyl-4-phenylbutan-2-ol, 2-methyl-3-phenylpropan-2-ol, methyl salicylate, 3-methyl-5-(2,2,3,-trimethyl-3-cyclopenten-1-yl)-4-penten-2-ol, 2-methyl-2-vinyl-5-(1-hydroxy-1-methyl ethyl)-3,4-dihydrofuran, myrtenol, neohesperidin dihydrochalcone, neomenthol, nerol, nerolidol, trans-2-cis-6-nonadienol, 1,3-nonanediol acetate, nonadyl, 2-nonanol, cis-6-nonen-1-ol, trans-2-nonen-1-ol, nonyl alcohol, 1-octanol, 2-octanol, 3-octanol, cis-3-octen-1-ol, cis-2-octen-1-ol, trans-2-octen-1-ol, cis-6-octen-1-ol, cis-octen-1-ol, 1-octen-3-ol, oleyl alcohol, patchouli alcohol, 3-pentanol, n-pentanol, 2-pentanol, 1-penten-1-ol, cis-2-penten-1-ol, perillyl alcohol, 2-phenoxyethanol arabinogalactan, α-phenethyl alcohol, phenethyl salicylate, phenol, phenylacetaldehyde glyceryl acetal, 3-phenyl-1-pentanol, 5-phenyl-1-pentanol, 1-phenyl-1-pentanol, 1-phenyl-2-pentanol, 1-phenyl-3-methyl-1-pentanol, phytol, pinacol, polyalkylene glycols, polysorbate 20, polysorbate 60, polysorbate 80, prenol, n-propanol, propenyl guaethol, propylene glycol, 2-propylphenol, 4-propylphenol, resorcinol, retinol, salicylaldehyde, sorbitan monostearate, sorbitol, stearyl alcohol, syringealdehyde, α-terpineol, tetrahydrogeraniol, tetrahydrolinalool, tetrahydromyrcenol, thymol, triethyl citrate, 1,2,6-trihydroxyhexane, p-α,α-trimethylbenzyl alcohol, 2-(5,5,6-trimethylbicyclo[2.2.1]hept-2-ylcyclohexanol, 5-(2,2,3-trimethyl-3-cyclopentenyl)-3-methylpentan-2-ol, 3,7,-11-trimethyl-2,6,10-dodecatrien-1-ol, 3,7,11-trimethyl-1,6,10-dodecatrien-3-ol, 3,5,5-trimethyl-1-hexanol, 10undecen-1-ol, undecyl alcohol, vanillin, o-vanillin, vanillyl butyl ether, 4-vinylphenol, 2,5-xylenol, 2,6-xylenol, 3,5-xylenol, 2,4-xylenol, and xylose or from the group of carbonyl-containing compounds consisting of 4-acetoxy-3-pentyl-tetrahydropyran, allyl cinnamate, allyl 2-ethylbutyrate, allyl cyclohexanepropionate, allyl heptanoate, allyl hexanoate, allyl isovalerate, allyl nonanoate, allyl octanoate, allyl phenoxyacetate, allyl phenylacetate, allyl propionate, α-amylcinnamyl acetate, amyl octanoate, anisyl acetate, anisylphenyl acetate, benzyl acetate, benzyl acetoacetate, benzyl butyrate, benzyl cinnamate, benzyl isobutyrate, benzyl isovalerate, benzyl phenylacetate, benzyl propionate, bornyl acetate, bornyl isovalerate, bornyl valerate, butyl acetate, butyl butyrate, butyl butyryllactate, 4-t-butylcyclohexyl acetate, butyl heptanoate, butyl hexanoate, butyl isobutyrate, butyl isovalerate, butyl laurate, butyl propionate, butyl stearate, 3-butylidenephthalide, butyl 2-methylbutyrate, butyl 10-undeceneoate, γ-butyrolactone, carvyl acetate, carvyl propionate, caryophyllene acetate, cedryl acetate, trans-cinnamyl acetate, trans-cinnamyl butyrate, cinnamyl cinnamate, cinnamyl isobutyrate, citronellyl acetate, citronellyl butyrate, citronellyl isobutyrate, citronellyl propionate, citronellyl valerate, cyclohexaneethyl acetate, cyclohexyl acetate, cyclohexyl butyrate, cyclohexyl isovalerate, cyclohexyl propionate, δ-decalactone, ε-decalactone, γ-decalactone, 4-decanolide, decyl acetate, decyl butyrate, decyl propionate, diethyl malonate, diethyl sebacate, diethyl succinate, dihydrocarvyl acetate, dihydrocoumarin, dihydromyrcenyl acetate, dihydro-nor-dicyclopentadienyl acetate, dihydroterpinyl acetate, 3,7-dimethyl-1,6-octadien-3-yl acetate, 3,7-dimethyl-1,6-octadien-3-yl propionate, 3,7-dimethyloctan-3-yl acetate, α,α-dimethylphenethyl acetate, α,α-dimethylphenethyl butyrate, 6,10-dimethyl-5,9-undecadien-2-yl acetate, δ-dodecalactone, ε-dodecalactone, γ-dodecalactone, ethyl acetate, ethyl acetoacetate, ethyl 6-acetoxyhexanoate, ethyl 2-acetyl-3-phenylpropionate, ethyl benzoylacetate, 2-ethylbutyl acetate, ethyl butyrate, ethyl cinnamate, ethyl cyclohexanepropionate, ethyl decanoate, ethylene brassylate, ethyl 2-ethyl-6,6-dimethyl-2-cyclohexenecarboxylate, ethyl 2,3-epoxybutyrate, ethyl 2-methyl-4-penteneoate, ethyl heptanoate, ethyl hexanoate, ethyl trans-3-hexenoate, 2-ethylhexyl acetate, ethyl isobutyrate, ethyl isovalerate, ethyl laurate, ethyl 2-mercaptopropionate, ethyl 3-mercaptopropionate, ethyl 2-methylbutyrate, ethyl 2-methylpentanoate, ethyl (methylthio)acetate, ethyl myristate, ethyl nonanoate, ethyl octanoate, ethyl palmitate, ethyl phenylacetate, ethyl 3-phenylpropionate, ethyl 3-phenyl-2,3-epoxybutyrate, ethyl 3-phenylpropionate, ethyl propionate, ethyl stearate, ethyl 2,3,6,6-tetramethyl-2-cyclohexencarboxylate, ethyl (p-tolyloxy)acetate, ethyl undecanoate, ethyl valerate, eugenyl acetate, fenchyl acetate, geranyl acetate, geranyl butyrate, geranyl phenylacetate, geranyl propionate, guaiacyl phenylacetate, guaicwood acetate, γ-heptalactone, heptyl acetate, heptyl butyrate, heptyl isobutyrate, ω-6-hexadecenlactone, δ-hexylactone, γ-hexylactone, 3-hexenyl acetate, cis-3-hexenyl 2-methylbutanoate, cis-3-hexenyl cis-3-hexenoate, cis-3-hexenyl phenylacetate, trans-2-hexenyl acetate, hexyl acetate, hexyl butyrate, hexyl hexanoate, hexyl isobutyrate, hexyl propionate, hexyl 2-methybutanoate, hexyl 3-methylbutanoate, hexyl phenylacetate, isoamyl acetate, isoamyl acetoacetate, isoamyl butyrate, isoamyl cinnamate, isoamyl hexanoate, isoamyl isobutyrate, isoamyl isovalerate, isoamyl laurate, isoamyl nonanoate, isoamyl octanoate, isoamyl phenylacetate, isoamyl propionate, isobornyl acetate, isobornyl propionate, isobutyl acetate, isobutyl butyrate, isobutyl cinnamate, isobutyl hexanoate, isobutyl isobutyrate, isobutyl 2-methylbutyrate, isobutyl propionate, isoeugenyl acetate, isopropyl cinnamate, isobutyl phenylacetate, isopropyl acetate, isopropyl butyrate, isopropyl isobutyrate, isopropyl myristate, isopropyl palmitate, isopropyl phenylacetate, lauryl acetate, linalyl acetate, linalyl butyrate, linalyl isovalerate, menthalactone, menthyl acetate, menthyl cyclohexanecarboxylate, menthyl isovalerate, 4-methoxybenzyl acetate, 4-methoxybenzyl propionate, 2-methoxyphenyl acetate, 2-methoxy-4-(1-propenyl)phenyl acetate, methyl acetate, α-methylbenzyl acetate, α-methylbenzyl butyrate, α-methylbenzyl propionate, 2-methylbutyl acetate, 2-methylbutyl butyrate, 2-methylbutyl isovalerate, 3-methylbutyl 2-methylbutanoate, 2-methylbutyl 2-methylbutanoate, methyl p-t-butylphenylacetate, methyl butyrate, methyl cinnamate, methyl decanoate, methyl heptanoate, methyl hexanoate, methyl isobutyrate, methyl isovalerate, methyl laurate, methyl N-2-methyl-3-(4-t-butylphenylpropylidene) anthranilate, methyl (methylthio)acetate, methyl 2-(methylthio) propionate, methyl myristate, methyl nonanoate, methyl octanoate, methyl palmitate, 4-(4-methyl-3-pentenyl)-3-cyclohexenylmethyl acetate, methyl 2-methylbutyrate, 2-methyl-6-methylen-7-octen-2-yl acetate, methyl 4-methylvalerate, methyl 2-methylpentanoate, methyl phenoxyacetate, 4-methylphenyl phenylacetate, 2-methyl-3-phenylpropan-2-yl acetate, methyl 3-phenylpropionate, methyl propionate, 2-methylpropyl phenylacetate, methyl phenylacetate, 2-methyl-3-phenylpropan-2-yl acetate, methyl stearate, methyl (p-tolyloxy)acetate, methyl 9-undecenoate, methyl valerate, myrtenyl acetate, neryl acetate, neryl butyrate, neryl isobutyrate, δ-nonalactone, α-nonalactone, 1,3-nonanediol diacetate, nonyl acetate, nopyl acetate, octahydrocoumarin, γ-octalactone, 1-octen-3-yl acetate, 1-octen-3-yl butyrate, octyl acetate, octyl butyrate, octyl isobutyrate, octyl isovalerate, octyl octanoate, octyl propionate, oxacycloheptadec-10-en-2-one, ω-pentadecalactone, pentyl acetate, pentyl butyrate, pentyl hexanoate, pentyl octanoate, phenethyl acetate, phenethyl butyrate, phenethyl cinnamate, phenethyl hexanoate, phenethyl isobutyrate, phenethyl isovalerate, phenethyl 2-methylbutyrate, phenethyl 2-methylbutyrate, phenethyl 2-methylpropionate, phenethyl octanoate, phenethyl phenylacetate, phenethyl propionate, phenoxyethyl propionate, 2-phenoxyethyl 2-methylpropionate, 3-phenyl-2-propenyl propionate, 3-phenylpropyl acetate, 2-phenylpropyl butyrate, 2-phenylpropyl isobutyrate, 2-phenylpropyl isovalerate, piperonyl acetate, piperonyl isobutyrate, prenyl acetate, propyl acetate, propyl butyrate, propyl heptanoate, propyl hexanoate, 3-propylidenephthalide, propyl isobutyrate, propyl propionate, propyl phenylacetate, sucrose octaacetate, terpinyl acetate, terpinyl butyrate, terpinyl isobutyrate, terpinyl propionate, tetrahydrofurfuryl acetate, tetrahydrofurfuryl butyrate, tetrahydrofurfuryl propionate, tetrahydrolinalyl acetate, 2,6,6,8-tetramethyl-tricyclo[5.3.1.0(1.5)]udecan-8-yl acetate, p-tolyl acetate, p-tolyl isobutyrate, p-tolyl phenylacetate, triacetin, tributyl acetylcitrate, tributyrin, tripropionin, 3,5,5-trimethylhexyl acetate, δ-undecalactone, γ-undecalactone, γ-valerolactone, vanillin acetate, vanillyl isobutyrate, 1-vinyl-2-(1-methylpropyl)cyclohexyl acetate, whiskey lactone, butyraldehyde, citronellal, decanal, cis-4-decenal, trans-4-decenal, 2,4-dimethyl-3-cyclohexen-1-carbaldehyde, 2,6-dimethyl-5-heptenal, 3,7-dimethyloctanal, 2-ethylbutyraldehyde, glutaric dialdehyde, heptanal, cis-4-heptenal, hexanal, hydrocinnamaldehyde, isobutyraldehyde, 3-(p-isopropylphenyl)propionaldehyde, isovaleraldehyde, lauric aldehyde, 2-methylbutyraldehyde, 2-methyl-3-(p-isopropylphenyl)propionaldehyde, 2-methylpentanal, 4-(4-methyl-3-pentenyl)-3-cyclohexen-1-carbaldehyde, 4-methylphenylacetaldehyde, 3-(methylthio)butanal, 2-methyl-4-(2,6,6-trimethyl-2-cyclohexen-1-yl)butanal, 2-methylundecanal, nonanal, cis-6-nonenal, octanal, phenylacetaldehyde, 2-phenylpropionaldehyde, 3-phenylpropionaldehyde, propionaldehyde, p-tolylacetaldehyde, tridecanal, 2,4,6-trimethyl-3-cyclohexen-1-carbaldehyde, 2,6,10-trimethyl-9-undecanal, 7undecenal, 8-undecenal, 9-undecenal, 10-undecenal, valeraldehyde, acetanisole, 1'-acetonaphthone, 2'-acetonaphthone, acetone, acetophenone, 2-acetoxy-2,5-dimethyl-3 (2H)furanone, 2-acetylcyclopentanone, 4-acetyl-1,1-dimethyl-6-t-butylindan, 7-acetyl-1,1,3,4,4,6-hexamethylindan, 2-acetyl-2-thiazoline, 6-acetyl-1,1,2,4,4,7-hexamethyl tetralin, allyl α-ionone, benzylideneacetone, 2,3-butanedione, 2-sec-butylcyclohexanone, 5-t-butyl-3,5-dinitro-2,6-dimethylacetophenone, butyrophenone, camphor, 2-decanone, 3-decanone, 3-decen-2-one, dihydrocarvone, dihydro-β-ionone, dihydrojasmone, 4,5-dihydro-3 (2H)-thiophenone, 2',4'-dimethylacetophenone, 3,4-dimethyl-1,2-cyclopentadione, 3,5-dimethyl-1,2-cyclopentadione, 2,6-dimethyl-4-heptanone, 1,3-diphenyl-2-propanone, 4-(1-ethoxyvinyl)-3,3,5,5-tetramethylcyclohexanone, p-ethylacetophenone, ethyl vinyl ketone, geranylacetone, 2,3-heptanedione, 2-heptanone, 3-heptanone, 4-heptanone, 3,4-hexanedione, 3-hexanone, 4-hexen-3-one, 2-hexylidene cyclopentanone, α-ionone, β-ionone, 4-isobutyl-2,6-dimethyl-3,5-dinitroacetophenone, isophorone, 6-isopropyldecahydro-2-naphthone, cis-jasmone, livescone, 4-methoxyacetophenone, 4-(p-methoxyphenyl)-2-butanone, 4'-methylacetophenone, 3-methyl-1,2-cyclohexanedione, 3-methyl-2-cyclohexen-1-one, 2-(2-(4-methyl-3-cylcohexen-1-yl)propyl)cyclopentanone, 3-methyl-2-cyclopenten-1-one, methyl dihydrojasmonate, methyl ethyl ketone, 2-methyl-3-heptanone, 5-methyl-2-hepten-4-one, 6-methyl-5-hepten-2-one, 5-methyl-α-ionone, 1-(2-methyl-5-isopropyl-2-cyclohexenyl)-1-propanone, 4-methyl-2-pentanone, 3-methyl-2-(2-pentenyl)-2-cyclopenten-1-one, 4-methyl-1-phenyl-2-pentanone, 2-methyltetrahydrofuran-3-one, 2-methyltetrahydrothiophen-3-one, 2-nonanone, 3-nonanone, 2-octanone, 3-octanone, 1-octen-3-one, 3-octen-2-one, 4-oxoisophorone, 2-pentadecanone, 2,3-pentanedione, 2-pentanone, 3-pentanone, 3-penten-2-one, 1-phenyl-1,2-propandione, propiophenone, pulegone, 2-tridecanone, 2,2,6trimethylcyclohexanone, 4-(2,6,6-trimethyl-2-cylcohexen-1-yl)-3-methyl-3-buten-2-one, 2-undecanone, and 6-undecanone.

The active-releasing compounds of the present invention are particularly suited to incorporation into personal care products to impart a desirable and long lasting effect to the products. Suitable uses include but are not limited to deodorants, antiperspirants, insect repellants, skin creams, facial creams, hair care products such as shampoos, mousses, styling gels, protective creams, shaving creams, after shave, cologne, perfume, color cosmetics such as lipsticks, foundations, blushes, makeup, and mascara; and other cosmetic formulations where other silicon-containing components have been added and where it is desirable to impart a certain effect. Incorporation of small amounts of the compositions of the present invention into fragrance products such as shaving lotions, colognes, toilet water, and perfumes can impart a desirable long lasting fragrance to these products. Further, the siloxanes of the present invention may be incorporated into other products where it is desirable to mask unpleasant odors with a pleasant fragrance, for example household cleaning products such as waxes and polishes, automobile cleaning products such as waxes and polishes, detergents, textile coatings, paints, varnishes and the like, subject to the limitation that the siloxane of the present invention be compatible or capable of being rendered compatible with the product in which it is incorporated.

EXPERIMENTAL

EXAMPLE 1

In a glass roundbottom flask, silane V (19.9 g, 0.083 mol) was charged and stirred for 15 min. A 10.9% solution of Pt(0) in divinyltetramethylsiloxane (15 mg of solution, 100 ppm Pt) was added. Tetramethylcyclotetrasiloxane (5.07 g, 0.083 mol hydride) was then added to the reaction mixture over 30 min. A slight exotherm was observed. The reaction mixture was then heated to 65° C. and maintained at said temperature for 5 h. The volatiles were then stripped under vacuum (70° C., 0.5 mm Hg) for 1.5 h. The brown product was mixed with Celite and filtered to give 17.9 g of a straw colored fluid (71.6%).

EXAMPLE 2

In a glass roundbottom flask, silane VI (19.3 g, 0.093 mol) was charged and stirred. A 10.9% solution of Pt(0) in divinyltetramethylsiloxane (17 mg of solution, 74 ppm Pt) was added. Tetramethylcyclotetrasiloxane (5.71 g, 0.093 mol hydride) was then added to the reaction mixture over 25 min. The reaction mixture was then heated to 65° C. and maintained at said temperature for 6 h. The volatiles were then stripped under vacuum (70° C., 0.5 mm Hg) for 1.5 h. The product was mixed with Celite and filtered to give 15.2 g of pale brown fluid (60.8%).

EXAMPLE 3

In a glass roundbottom flask, silane VII (9.80 g, 0.041 mol) was charged and stirred. A 10.9% solution of Pt(0) in divinyltetramethylsiloxane (14 mg of solution, 200 ppm Pt) was added. Tetramethylcyclotetrasiloxane (2.51 g, 0.041 mol hydride) was then added to the reaction mixture over 25 min. A significant exotherm was observed. The reaction mixture was then heated to 70° C. and maintained at said temperature for 2.5 h. The product was filtered to give 11.0 g of a straw colored fluid (89.4%).

EXAMPLE 4

In a glass roundbottom flask, silane VIII (16.41 g, 0.060 mol) was charged and stirred. A 10.9% solution of Pt(0) in divinyltetramethylsiloxane (21 mg of solution, 200 ppm Pt) was added, and the mixture was stirred for 15 min. Tetramethylcyclotetrasiloxane (3.61 g, 0.060 mol hydride) was then added to the reaction mixture over 25 min. The reaction mixture was then heated to 70° C. and maintained at said temperature for 2.5 h. The product was stripped (75° C., 0.5 mm Hg) for 1.5 h then filtered to give 18.1 g of yellow fluid (90.5%).

EXAMPLE 5

In a glass roundbottom flask, silane IX (16.78 g, 0.054 mol) was charged along with a 10.9% solution of Pt(0) in divinyltetramethylsiloxane (14 mg of solution, 150 ppm Pt). The mixture was stirred for 15 min. Tetramethylcyclotetrasiloxane (3.23 g, 0.054 mol hydride) was then added to the reaction mixture over 25 min; the solution increased in viscosity. The reaction mixture was then heated to 60° C. and maintained at said temperature for 80 min. The product was stripped (70° C., 3 mm Hg) for 1 h then filtered to give 16.5 g of pale orange fluid (82.5%).

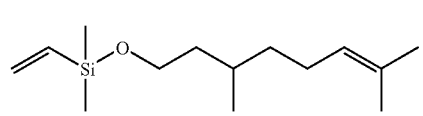

V

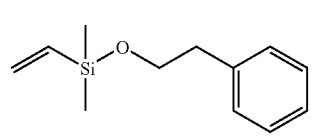

VI

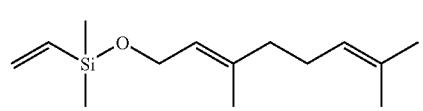

VII

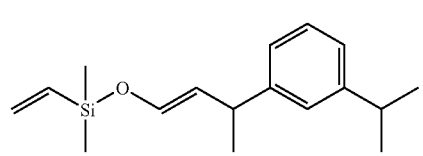

VIII

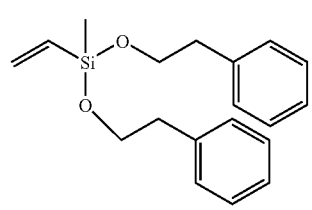

IX

EXAMPLES 6-10

Hydrolysis of Products from Examples 1-5, Respectively

The general procedure for hydrolysis is as follows:

A solution of the active ingredient-functional silicone (1.0 g), tetrahydrofuran (10 g), and bibenzyl internal standard (0.4 g) was prepared. The solution was analyzed by gas chromatography, then 0.50 mL of 1% (wt.) aqueous sodium hydroxide solution was added (except for example 9, in which 0.125 mL of 1% aqueous sodium hydroxide solution was used). The mixture was stirred and periodically sampled for gas chromatography analysis. Tables 1-5 demonstrate the release profiles determined in examples 6-10, respectively.

TABLE 1

Hydrolyis of product from example 1.

| Time (h) | Relative citronellol concentration |
|---|---|
| 0.00 | 0.042 |
| 0.92 | 0.077 |
| 8.92 | 0.145 |
| 22.58 | 0.198 |
| 29.33 | 0.220 |
| 47.00 | 0.248 |
| 55.00 | 0.258 |
| 70.75 | 0.282 |
| 78.08 | 0.283 |
| 93.92 | 0.298 |

TABLE 2

Hydrolyis of product from example 2.

| Time (h) | Relative phenethyl alcohol concentration |
|---|---|
| 0.00 | 0.025 |
| 1.33 | 0.102 |
| 9.33 | 0.253 |
| 23.00 | 0.418 |
| 29.75 | 0.450 |
| 47.50 | 0.532 |
| 55.50 | 0.557 |
| 71.25 | 0.604 |
| 78.50 | 0.614 |
| 94.42 | 0.639 |

TABLE 3

Hydrolysis of product from example 3.

| Time (h) | Relative geraniol concentration |
|---|---|
| 0.00 | 0.083 |
| 0.50 | 0.097 |
| 6.00 | 0.261 |
| 25.42 | 0.429 |
| 45.83 | 0.530 |
| 53.75 | 0.559 |
| 70.83 | 0.600 |
| 77.50 | 0.608 |
| 94.08 | 0.642 |

TABLE 4

Hydrolysis of product from example 4.

| Time (h) | Relative 3-methyl-3-(meta-ispropylphenyl)propionaldehyde concentration |
|---|---|
| 0.00 | 0.111 |
| 1.00 | 1.142 |
| 6.42 | 1.109 |
| 25.92 | 1.007 |
| 46.33 | 0.954 |
| 54.25 | 0.932 |
| 71.25 | 0.913 |
| 78.00 | 0.900 |
| 94.50 | 0.884 |

TABLE 5

Hydrolysis of product from example 5.

| Time (h) | Relative phenethyl alcohol concentration |
|---|---|
| 0.00 | 0.050 |
| 1.42 | 0.344 |
| 6.92 | 0.791 |
| 26.42 | 1.253 |
| 46.75 | 1.368 |
| 54.83 | 1.389 |
| 71.75 | 1.418 |
| 78.50 | 1.439 |
| 95.00 | 1.451 |

EXAMPLEs 11-12

Hydrolysis of Products from Examples 2 and 5, Respectively

The general procedure for hydrolysis is as follows:

A 3.3 cm by 3.3 cm swatch of untreated cotton cloth was soaked with each material such that the molar equivalents of active ingredient were equal between all of the samples. Each swatch was kept in a small aluminum pan, and all of the pans were kept in an open-top box in the same room at ambient temperature and humidity. The samples were smelled at timed intervals and rated for strength of scent (0=no scent, 5=same strength as pure active ingredient from the bottle). Data are presented in Tables 6 and 7. In example 11 (Table 6), it can be seen that the cloth treated with the siloxane derivative of the present invention release a stronger odor for a longer period of time. In example 12 (Table 7), it can be seen that the cloth treated with the siloxane derivative exhibits a more consistent degree of odor over time.

TABLE 6

Relative odor of fabric swatches (Example 11).

| Hours | Control | Siloxane from Ex. 2 |
|---|---|---|
| 0.0 | 5 | 5 |
| 5.0 | 4 | 4 |
| 21.5 | 4 | 4 |
| 28.9 | 3 | 4 |
| 46.3 | 3 | 4 |
| 52.8 | 3 | 4 |
| 78.1 | 3 | 4 |
| 164.3 | 3 | 4 |

TABLE 6-continued

Relative odor of fabric swatches (Example 11).

| Hours | Control | Siloxane from Ex. 2 |
|---|---|---|
| 215.3 | 2 | 3 |
| 237.1 | 1 | 2 |

TABLE 7

Relative odor of fabric swatches (Example 12).

| Hours | Control | Siloxane from Ex. 5 |
|---|---|---|
| 0.0 | 5 | 3 |
| 5.0 | 4 | 3 |
| 21.5 | 4 | 3 |
| 28.9 | 3 | 3 |
| 46.3 | 3 | 3 |
| 52.8 | 3 | 3 |
| 78.1 | 3 | 3 |
| 164.3 | 3 | 2 |
| 215.3 | 2 | 2 |
| 237.1 | 1 | 2 |

Having described the invention that which is claimed is:

1. An active ingredient-releasing cyclic siloxane selected from the group of siloxanes having the formulas:

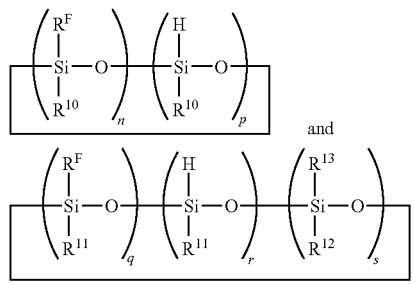

and where $R^{10}$, $R^{11}$, $R^{12}$, and $R^{13}$ are each independently selected from the group of monovalent $C_1$-$C_{24}$ hydrocarbon radicals, the subscripts n and q are each independently greater than or equal to 1, the subscripts p, r, and s are each independently equal to or greater than 0 with the proviso that n+p must be equal to or greater than 3 and that q+r+s must be equal to or greater than 3; where $R^F$ has the formula $(R^1O)_a(R^2O)_b(R^3O)_c(R^4)_d(R^5)_e SiR^U$ with $R^U$ a $C_2$-$C_{40}$ divalent hydrocarbon radical and $R^4$ and $R^5$ independently selected from the group consisting of monovalent hydrocarbon radicals having from one to forty carbon atoms, the subscript a has a value ranging from 1 to 3 and the subscripts b, c, d, and e have values ranging from 0 to 2 subject to the limitation that a+b+c+d+e=3, where each $R^1O$, $R^2O$ and $R^3O$ are independently selected from the group of conjugate bases consisting of conjugate bases derived from the group of alcohol active ingredients consisting of $R^1OH$, $R^2OH$, and $R^3OH$ where $R^1$, $R^2$ and $R^3$ are independently monovalent hydrocarbon radicals having from four to one hundred carbon atoms and the group of conjugate bases derived from the group of carbonyl active ingredients having the structure:

$$R^7-C(R^8)=C(O-)-R^9$$

where
$R^7$, $R^8$, and $R^9$ are each independently selected from the group consisting of hydrogen and monovalent hydrocarbon radicals having from one to one hundred carbon atoms.

2. The active ingredient-releasing cyclic siloxane of claim 1 having the formula:

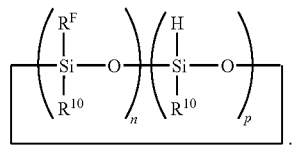

3. The active ingredient-releasing cyclic siloxane of claim 2 wherein $R^F$ has the formula $(R^1O)_a(R^2O)_b(R^3O)_c(R^4)_d(R^5)_d SiR^U$ with $R^U$ a $C_2$-$C_{40}$ divalent hydrocarbon radical and $R^4$ and $R^5$ independently selected from the group consisting of monovalent hydrocarbon radicals having from one to forty carbon atoms, the subscript a has a value ranging from 1 to 3 and the subscripts b, c, d, and e have values ranging from 0 to 2 subject to the limitation that a+b+c+d+e=3, where each $R^1O$, $R^2O$ and $R^3O$ are independently selected from the group of conjugate bases consisting of conjugate bases derived from the group of alcohol active ingredients consisting of $R^1OH$, $R^2OH$, and $R^3OH$.

4. The active ingredient-releasing cyclic siloxane of claim 3 wherein the alcohol active ingredients $R^1OH$, $R^2OH$, and $R^3OH$ are fragrant alcohols.

5. The active ingredient-releasing cyclic siloxane of claim 4 wherein the fragrant alcohols, $R^1OH$, $R^2OH$, and $R^3OH$ are selected from the group of fragrant alcohols consisting of acetovanillone, allyl amylglycolate, allyl isoamylglycolate, α-amylcinammyl alcohol, anisyl alcohol, benzoin, benzyl alcohol, benzyl salicylate, 1-butanol, butylated hydroxytoluene, butyl lactate, 2-t-butyl-5-methylphenol, 2-t-butyl-6-methylphenol, carvacrol, carveol, 4-carvomenthenol, cedrol, cetyl alcohol, cinnamic alcohol, citronellol, o-cresol, m-cresol, p-cresol, crotyl alcohol, decahydro-2-naphthol, 1-decanol, 1-decen-3-ol, 9-decen-1-ol, diethyl malate, diethyl tartrate, dihydrocarveol, dihydromyrcenol, 2,6-diisopropylphenol, dimethicone copolyol, 2,6-dimethoxyphenol, 1,1-dimethoxy-3,7-dimethyloctan-7-ol, 2,6-dimethyl-4-heptanol, 2,6-dimethylheptan-2-ol, 6,8-dimethyl-2-nonanol, 3,7-dimethyl-2,6-octadien-1-ol, 3,7-dimethyl-1,6-octadien-3-ol, 3,7-dimethyl-1-octanol, 3,7-dimethyl-3-octanol, 3,7-dimethyl-6-octen-1-ol, 3,7-dimethyl-7-octen-1-ol, dimetol, 2-ethylfenchol, 4-ethylguaiacol, 2-ethyl-1-hexanol, ethyl 2-hydroxybenzoate, ethyl 3-hydroxybutyrate, 3-ethyl-2-hydroxy-2-cyclopenten-1-one, ethyl 2-hydroxycaproate, ethyl 3-hydroxyhexanoate, ethyl lactate, ethyl maltol, p-ethylphenol, ethyl salicylate, eugenol, farnesol, fenchyl alcohol, geraniol, glucose petaacetate, glycerol, glyceryl monostearate, guaiacol, 1-heptanol, 2-heptanol, 3-heptanol, cis-4-heptenol, cis-3-heptenol, n-hexanol, 2-hexanol, 3-hexanol, cis-2-hexenol, cis-3-hexenol, trans-3-hexenol, 4-hexenol, cis-3-hexenyl hydrocinnamyl alcohol, 2-hydroxybenzoate, 2-hydroxyacetophenone, 4-hydroxybenzyl alcohol, 3-hydroxy-2-butanone, hydroxycitronellal, 4-(4-hydroxy-3-methoxyphenyl)-2-butanone, 2-hydroxy-3-methyl-2-cyclopenten-1-one, 4-(p-hydroxyphenyl)-2-butanone, 2-hydroxy-3,5,5-trimethyl-2-cyclohexenone, δ-isoascorbic acid, isoborneol, isoeugenol, isophytol, isopropyl alcohol, p-isopropylbenzyl alcohol, 4-isopropylcylcohexanol, 3-isopropylphenol, 4-isopropylphenol, 2-isopropylphenol, isopulegol, lauryl alcohol, linalool, maltol, menthol, 4-methoxybenzyl alcohol, 2-methoxy-4-methylphenol, 2-methoxy-4propylphenol, 2-methoxy-4-vinylphenol, α-methylbenzyl alcohol, 2-methylbutanol, 3-methyl-2-butanol, 3-methyl-2-buten-1-ol, 2-methyl-3-buten-2-ol, methyl 2,4-dihydroxy-3,6-dimethylbenzoate, 4-methyl-2,6-dimethoxyphenol, methyl N-3,7-dimethyl-7-hydroxyoctylideneanthranilate, methyl 3-hydroxyhexanoate, 6-methyl-5-hepten-2-ol, 2-methylpentanol, 3-methyl-3-pentanol, 2-methyl-4-phenylbutan-2-ol, 2-methyl-3-phenylpropan-2-ol, methyl salicylate, 3-methyl-5-(2,2,3,-trimethyl-3-cyclopenten-1-yl)-4-penten-2-ol, 2-methyl-2-vinyl-5-(1-hydroxy-1-methyl ethyl)-3,4-dihydrofuran, myrtenol, neohesperidin dihydrochalcone, neomenthol, nerol, nerolidol, trans-2-cis-6-nonadienol, 1,3-nonanediol acetate, nonadyl, 2-nonanol, cis-6-nonen-1-ol, trans-2-nonen-1-ol, nonyl alcohol, 1-octanol, 2-octanol, 3-octanol, cis-3-octen-1-ol, cis-2-octen-1-ol, trans-2-octen-1-ol, cis-6-octen-1-ol, cis-octen-1-ol, 1-octen-3-ol, oleyl alcohol, patchouli alcohol, 3-pentanol, n-pentanol, 2-pentanol, 1-penten-1-ol, cis-2-penten-1-ol, perillyl alcohol, 2-phenoxyethanol arabinogalactan, β-phenethyl alcohol, phenethyl salicylate, phenol, phenylacetaldehyde glyceryl acetal, 3-phenyl-1-pentanol, 5-phenyl-1-pentanol, 1-phenyl-1-pentanol, 1-phenyl-2-pentanol, 1-phenyl-3-methyl-1-pentanol, phytol, pinacol, polyalkylene glycols, polysorbate 20, polysorbate 60, polysorbate 80, prenol, n-propanol, propenyl guaethol, propylene glycol, 2-propylphenol, 4-propylphenol, resorcinol, retinol, salicylaldehyde, sorbitan monostearate, sorbitol, stearyl alcohol, syringealdehyde, α-terpineol, tetrahydrogeraniol, tetrahydrolinalool, tetrahydromyrcenol, thymol, triethyl citrate, 1,2,6-trihydroxyhexane, p-α,α-trimethylbenzyl alcohol, 2-(5,5,6-trimethylbicyclo[2.2.1]hept-2-ylcyclohexanol, 5-(2,2,3-trimethyl-3-cyclopentenyl)-3-methylpentan-2-ol, 3,7,-11-trimethyl-2,6,10-dodecatrien-1-ol, 3,7,11-trimethyl-1,6,10-dodecatrien-3-ol, 3,5,5-trimethyl-1-hexanol, 10-undecen-1-ol, undecyl alcohol, vanillin, o-vanillin, vanillyl butyl ether, 4-vinylphenol, 2,5-xylenol, 2,6-xylenol, 3,5-xylenol, 2,4-xylenol, and xylose.

6. The active ingredient-releasing cyclic siloxane of claim 1 having the formula:

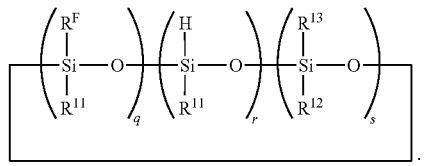

7. The active ingredient-releasing cyclic siloxane of claim 6 wherein $R^F$ has the formula $(R^1O)_a(R^2O)_b(R^3O)_c(R^4)_d(R^5)_e SiR^U$ with $R^U$ a $C_2$-$C_{40}$ divalent hydrocarbon radical and $R^4$ and $R^5$ independently selected from the group consisting of monovalent hydrocarbon radicals having from one to forty carbon atoms, the subscript a has a value ranging from 1 to 3 and the subscripts b, c, d, and e have values ranging from 0 to 2 subject to the limitation that a+b+c+d+e=3, where each $R^1O$, $R^2O$ and $R^3O$ are independently selected from the group of conjugate bases consisting of conjugate bases derived from the group of alcohol active ingredients consisting of $R^1OH$, $R^2OH$, and $R^3OH$.

8. The active ingredient-releasing cyclic siloxane of claim 7 wherein the alcohol active ingredients $R^1OH$, $R^2OH$, and $R^3OH$ are fragrant alcohols.

9. The active ingredient-releasing cyclic siloxane of claim 8 wherein the fragrant alcohols, $R^1OH$, $R^2OH$, and $R^3OH$ are selected from the group of fragrant alcohols consisting of acetovanillone, allyl amylglycolate, allyl isoamylglycolate, α-amylcinammyl alcohol, anisyl alcohol, benzoin, benzyl alcohol, benzyl salicylate, 1-butanol, butylated hydroxytoluene, butyl lactate, 2-t-butyl-5-methylphenol, 2-t-butyl-6-methylphenol, carvacrol, carveol, 4-carvomenthenol, cedrol, cetyl alcohol, cinnamic alcohol, citronellol, o-cresol, m-cresol, p-cresol, crotyl alcohol, decahydro-2-naphthol, 1-decanol, 1-decen-3-ol, 9-decen-1-ol, diethyl malate, diethyl tartrate, dihydrocarveol, dihydromyrcenol, 2,6-diisopropylphenol, dimethicone copolyol, 2,6-dimethoxyphenol, 1,1-dimethoxy-3,7-dimethyloctan-7-ol, 2,6-dimethyl-4-heptanol, 2,6-dimethylheptan-2-ol, 6,8-dimethyl-2-nonanol, 3,7-dimethyl-2,6-octadien-1-ol, 3,7-dimethyl-1,6-octadien-3-ol, 3,7-dimethyl-1-octanol, 3,7-dimethyl-3-octanol, 3,7-dimethyl-6-octen-1-ol, 3,7-dimethyl-7-octen-1-ol, dimetol, 2-ethylfenchol, 4-ethylguaiacol, 2-ethyl-1-hexanol, ethyl 2-hydroxybenzoate, ethyl 3-hydroxybutyrate, 3-ethyl-2-hydroxy-2-cyclopenten-1-one, ethyl 2-hydroxycaproate, ethyl 3-hydroxyhexanoate, ethyl lactate, ethyl maltol, p-ethylphenol, ethyl salicylate, eugenol, farnesol, fenchyl alcohol, geraniol, glucose petaacetate, glycerol, glyceryl monostearate, guaiacol, 1-heptanol, 2-heptanol, 3-heptanol, cis-4-heptenol, cis-3-heptenol, n-hexanol, 2-hexanol, 3-hexanol, cis-2-hexenol, cis-3-hexenol, trans-3-hexenol, 4-hexenol, cis-3-hexenyl hydrocinnamyl alcohol, 2-hydroxybenzoate, 2-hydroxyacetophenone, 4-hydroxybenzyl alcohol, 3-hydroxy-2-butanone, hydroxycitronellal, 4-(4-hydroxy-3-methoxyphenyl)-2-butanone, 2-hydroxy-3-methyl-2-cyclopenten-1-one, 4-(p-hydroxyphenyl)-2-butanone, 2-hydroxy-3,5,5-trimethyl-2-cyclohexenone, δ-isoascorbic acid, isoborneol, isoeugenol, isophytol, isopropyl alcohol, p-isopropylbenzyl alcohol, 4-isopropylcylcohexanol, 3-isopropylphenol, 4-isopropylphenol, 2-isopropylphenol, isopulegol, lauryl alcohol, linalool, maltol, menthol, 4-methoxybenzyl alcohol, 2-methoxy-4-methylphenol, 2-methoxy-4-propylphenol, 2-methoxy-4-vinylphenol, α-methylbenzyl alcohol, 2-methylbutanol, 3-methyl-2-butanol, 3-methyl-2-buten-1-ol, 2-methyl-3-buten-2-ol, methyl 2,4-dihydroxy-3,6-dimethylbenzoate, 4-methyl-2,6-dimethoxyphenol, methyl N-3, 7-dimethyl-7-hydroxyoctylideneanthranilate, methyl 3-hydroxyhexanoate, 6-methyl-5-hepten-2-ol, 2-methylpentanol, 3-methyl-3-pentanol, 2-methyl-4-phenylbutan-2-ol, 2-methyl-3-phenylpropan-2-ol, methyl salicylate, 3-methyl-5-(2,2,3,-trimethyl-3-cyclopenten-1-yl)-4-penten-2-ol, 2-methyl-2-vinyl-5-(1-hydroxy-1-methyl ethyl)-3,4-dihydrofuran, myrtenol, neohesperidin dihydrochalcone, neomenthol, nerol, nerolidol, trans-2-cis-6-nonadienol, 1,3-nonanediol acetate, nonadyl, 2-nonanol, cis-6-nonen-1-ol, trans-2-nonen-1-ol, nonyl alcohol, 1-octanol, 2-octanol, 3-octanol, cis-3-octen-1-ol, cis-2-octen-1-ol, trans-2-octen-1-ol, cis-6-octen-1-ol, cis-octen-1-ol, 1-octen-3-ol, oleyl alcohol, patchouli alcohol, 3-pentanol, n-pentanol, 2-pentanol, 1-penten-1-ol, cis-2-penten-1-ol, perillyl alcohol, 2-phenoxyethanol arabinogalactan, β-phenethyl alcohol, phenethyl salicylate, phenol, phenylacetaldehyde glyceryl acetal, 3-phenyl-1-pentanol, 5-phenyl-1-pentanol, 1-phenyl-1-pentanol, 1-phenyl-2-pentanol, 1-phenyl-3-methyl-1-pentanol, phytol, pinacol, polyalkylene glycols, polysorbate 20, polysorbate 60, polysorbate 80, prenol, n-propanol, propenyl guaethol, propylene glycol, 2-propylphenol, 4-propylphenol, resorcinol, retinol, salicylaldehyde, sorbitan monostearate, sorbitol, stearyl alcohol, syringealdehyde, α-terpineol, tetrahydrogeraniol, tetrahydrolnalool, tetrahydromyrcenol, thymol, triethyl citrate, 1,2,6-trihydroxyhexane, p-α,α-trimethylbenzyl alcohol, 2-(5,5,6-trimethylbicyclo[2.2.1]hept-2-ylcyclohexanol, 5-(2,2,3-trimethyl-3-cyclopentenyl)-3-methylpentan-2-ol, 3,7,-11-trimethyl-2,6,10-dodecatrien-1-ol, 3,7,11-trimethyl-1,6,10-dodecatrien-3-ol, 3,5,5-trimethyl-1-hexanol, 10-undecen-1-ol, undecyl alcohol, vanillin, o-vanillin, vanillyl butyl ether, 4-vinylphenol, 2,5-xylenol, 2,6-xylenol, 3,5-xylenol, 2,4-xylenol, and xylose.

10. The active ingredient-releasing cyclic siloxane of claim 2 wherein $R^F$ has the formula $(R^1O)_a(R^2O)_b(R^3O)_c(R^4)_d(R^5)_e SiR^U$ with $R^U$ a $C_2$-$C_{40}$ divalent hydrocarbon radical and $R^4$ and $R^5$ independently selected from the group consisting of monovalent hydrocarbon radicals having from one to forty carbon atoms, the subscript a has a value ranging from 1 to 3 and the subscripts b, c, d, and e have values ranging from 0 to 2 subject to the limitation that a+b+c+d+e=3, where each $R^1O$, $R^2O$ and $R^3O$ are independently selected from the group of conjugate bases consisting of conjugate bases derived from the group of conjugate bases derived from the group of carbonyl active ingredients having the structure:

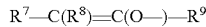

where $R^7$, $R^8$, and $R^9$ are each independently selected from the group consisting of hydrogen and monovalent hydrocarbon radicals having from one to one hundred carbon atoms.

11. The active ingredient-releasing cyclic siloxane of claim 10 wherein the carbonyl active ingredients are fragrant carbonyl active ingredients.

12. The active ingredient-releasing cyclic siloxane of claim 11 where the fragrant carbonyl active ingredients are selected from the group consisting of 4-acetoxy-3-pentyl-tetrahydropyran, allyl cinnamate, allyl 2-ethylbutyrate, allyl cyclohexanepropionate, allyl heptanoate, allyl hexanoate, allyl isovalerate, allyl nonanoate, allyl octanoate, allyl phenoxyacetate, allyl phenylacetate, allyl propionate, α-amylcinnamyl acetate, amyl octanoate, anisyl acetate, anisylphenyl acetate, benzyl acetate, benzyl acetoacetate, benzyl butyrate, benzyl cinnamate, benzyl isobutyrate, benzyl isovalerate, benzyl phenylacetate, benzyl propionate, bornyl acetate, bornyl isovalerate, bornyl valerate, butyl acetate, butyl butyrate, butyl butyryllactate, 4-t-butylcyclohexyl acetate, butyl heptanoate, butyl hexanoate, butyl isobutyrate, butyl isovalerate, butyl laurate, butyl propionate, butyl stearate, 3-butylidenephthalide, butyl 2-methylbutyrate, butyl 10-undeceneoate, γ-butyrolactone, carvyl acetate, carvyl propionate, caryophyllene acetate, cedryl acetate, trans-cinnamyl acetate, trans-cinnamyl butyrate, cinnamyl cinnamate, cinnamyl isobutyrate, citronellyl acetate, citronellyl butyrate, citronellyl isobutyrate, citronellyl propionate, citronellyl valerate, cyclohexaneethyl acetate, cyclohexyl acetate, cyclohexyl butyrate, cyclohexyl isovalerate, cyclohexyl propionate, δ-decalactone, ε-decalactone, γ-decalactone, 4-decanolide, decyl acetate, decyl butyrate, decyl propionate, diethyl malonate, diethyl sebacate, diethyl succinate, dihydrocarvyl acetate, dihydrocoumarin, dihydromyrcenyl acetate, dihydro-nor-dicyclopentadienyl acetate, dihydroterpinyl acetate, 3,7-dimethyl-1,6-octadien-3-yl acetate, 3,7-dimethyl-1,6-octadien-3-yl propionate, 3,7-dimethyloctan-3-yl acetate, α,α-dimethylphenethyl acetate, α,α-dimethylphenethyl butyrate, 6,10-dimethyl-5,9-undecadien-2-yl acetate, δ-dodecalactone, ε-dodecalactone, γ-dodecalactone, ethyl acetate, ethyl acetoacetate, ethyl 6-acetoxyhexanoate, ethyl 2-acetyl-3-phenylpropionate, ethyl benzoylacetate, 2-ethylbutyl acetate, ethyl butyrate, ethyl cinnamate, ethyl cyclohexanepropionate, ethyl decanoate, ethylene brassylate, ethyl 2-ethyl-6,6-dimethyl-2-cyclohexenecarboxylate, ethyl 2,3-epoxybutyrate, ethyl 2-methyl-4-penteneoate, ethyl heptanoate, ethyl hexanoate, ethyl trans-3-hexenoate, 2-ethylhexyl acetate, ethyl isobutyrate, ethyl isovalerate, ethyl laurate, ethyl 2-mercaptopropionate, ethyl 3-mercaptopropionate, ethyl 2-methylbutyrate, ethyl 2-methylpentanoate, ethyl (methylthio)acetate, ethyl myristate, ethyl nonanoate, ethyl octanoate, ethyl palmitate, ethyl phenylacetate, ethyl 3-phenylpropionate, ethyl 3-phenyl-2,3-epoxybutyrate, ethyl 3-phenylpropionate, ethyl propionate; ethyl stearate, ethyl 2,3,6,6-tetramethyl-2-cyclohexencarboxylate, ethyl (p-tolyloxy)acetate, ethyl undecanoate, ethyl valerate, eugenyl acetate, fenchyl acetate, geranyl acetate, geranyl butyrate, geranyl phenylacetate, geranyl propionate, guaiacyl phenylacetate, guaicwood acetate, γ-heptalactone, heptyl acetate, heptyl butyrate, heptyl isobutyrate, ω-6-hexadecenlactone, δ-hexylactone, γ-hexylactone, 3-hexenyl acetate, cis-3-hexenyl 2-methylbutanoate, cis-3-hexenyl cis-3-hexenoate, cis-3-hexenyl phenylacetate, trans-2-hexenyl acetate, hexyl acetate, hexyl butyrate, hexyl hexanoate, hexyl isobutyrate, hexyl propionate, hexyl 2-methybutanoate, hexyl 3-methylbutanoate, hexyl phenylacetate, isoamyl acetate, isoamyl acetoacetate, isoamyl butyrate, isoamyl cinnamate, isoamyl hexanoate, isoamyl isobutyrate, isoamyl isovalerate, isoamyl laurate, isoamyl nonanoate, isoamyl octanoate, isoamyl phenylacetate, isoamyl propionate, isobornyl acetate, isobornyl propionate, isobutyl acetate, isobutyl butyrate, isobutyl cinnamate, isobutyl hexanoate, isobutyl isobutyrate, isobutyl 2-methylbutyrate, isobutyl propionate, isoeugenyl acetate, isopropyl cinnamate, isobutyl phenylacetate, isopropyl acetate, isopropyl butyrate, isopropyl isobutyrate, isopropyl myristate, isopropyl palmitate, isopropyl phenylacetate, lauryl acetate, linalyl acetate, linalyl butyrate, linalyl isovalerate, menthalactone, menthyl acetate, menthyl cyclohexanecarboxylate, menthyl isovalerate, 4-methoxybenzyl acetate, 4-methoxybenzyl propionate, 2-methoxyphenyl acetate, 2-methoxy-4-(1-propenyl)phenyl acetate, methyl acetate, α-methylbenzyl acetate, α-methylbenzyl butyrate, α-methylbenzyl propionate, 2-methylbutyl acetate, 2-methylbutyl butyrate, 2-methylbutyl isovalerate, 3-methylbutyl 2-methylbutanoate, 2-methylbutyl 2-methylbutanoate, methyl p-t-butylphenylacetate, methyl butyrate, methyl cinnamate, methyl decanoate, methyl heptanoate, methyl hexanoate, methyl isobutyrate, methyl isovalerate, methyl laurate, methyl N-2-methyl-3-(4-t-butylphenylpropylidene) anthranilate, methyl (methylthio)acetate, methyl 2-(methylthio) propionate, methyl myristate, methyl nonanoate, methyl octanoate, methyl palmitate, 4-(4-methyl-3-pentenyl)-3-cyclohexenylmethyl acetate, methyl 2-methylbutyrate, 2-methyl-6-methylen-7-octen-2-yl acetate, methyl 4-methylvalerate, methyl 2-methylpentanoate, methyl phenoxyacetate, 4-methylphenyl phenylacetate, 2-methyl-3-phenylpropan-2-yl acetate, methyl 3-phenylpropionate, methyl propionate, 2-methylpropyl phenylacetate, methyl phenylacetate, 2-methyl-3-phenylpropan-2-yl acetate, methyl stearate, methyl (p-tolyloxy)acetate, methyl 9-undecenoate, methyl valerate, myrtenyl acetate, neryl acetate, neryl butyrate, neryl isobutyrate, δ-nonalactone, γ-nonalactone, 1,3-nonanediol diacetate, nonyl acetate, nopyl acetate, octahydrocoumarin, γ-octalactone, 1-octen-3-yl acetate, 1-octen-3-yl butyrate, octyl acetate, octyl butyrate, octyl isobutyrate, octyl isovalerate, octyl octanoate, octyl propionate, oxacycloheptadec-10-en-2-one, ω-pentadecalactone, pentyl acetate, pentyl butyrate, pentyl hexanoate, pentyl octanoate, phenethyl acetate, phenethyl butyrate, phenethyl cinnamate, phenethyl hexanoate, phenethyl isobutyrate, phenethyl isovalerate, phenethyl 2-methylbutyrate, phenethyl 2-methylbutyrate, phenethyl 2-methylpropionate, phenethyl octanoate, phenethyl phenylacetate, phenethyl propionate, phenoxyethyl propionation, 2-phenoxyethyl 2-methylpropionate, 3-phenyl-2-propenyl propionate, 3-phenylpropyl acetate, 2-phenylpropyl butyrate; 2-phenylpropyl isobutyrate, 2-phenylpropyl isovalerate, piperonyl acetate, piperonyl isobutyrate, prenyl acetate, propyl acetate, propyl butyrate, propyl heptanoate, propyl hexanoate, 3-propylidenephthalide, propyl isobutyrate, propyl propionate, propyl phenylacetate, sucrose octaacetate, terpinyl acetate, terpinyl butyrate, terpinyl isobutyrate, terpinyl propionate, δ-nonalactone, tetrahydrofurfuryl acetate, tetrahydrofurfuryl butyrate, tetrahydrofurfuryl propionate, tetrahydrolinalyl acetate, 2,6,6,8-tetramethyl-tricyclo[5.3.1.0 (1.5)]udecan-8-yl acetate, p-tolyl acetate, p-tolyl isobutyrate, p-tolyl phenylacetate, triacetin, tributyl acetylcitrate, tributyrin, tripropionin, 3,5,5-trimethylhexyl acetate, δ-undecalactone, γ-undecalactone, γ-valerolactone, vanillin acetate, vanillyl isobutyrate, 1-vinyl-2-(1-methylpropyl)cyclohexyl acetate, whiskey lactone, butyraldehyde, citronellal, decanal, cis-4-decenal, trans-4-decenal, 2,4-dimethyl-3-cyclohexen-1-carbaldehyde, 2,6-dimethyl-5-heptenal, 3,7-dimethyloctanal, 2-ethylbutyraldehyde, glutaric dialdehyde, heptanal, cis-4-heptenal, hexanal, hydrocinnamaldehyde, isobutyraldehyde, 3-(p-isopropylphenyl)propionaldehyde, isovaleraldehyde, lauric aldehyde, 2-methylbutyraldehyde, 2-methyl-3-(p-isopropylphenyl)propionaldehyde, 2-methylpentanal, 4-(4-methyl-3-pentenyl)-3-cyclohexen-1-carbaldehyde, 4-methylphenylacetaldehyde, 3-(methylthio)butanal, 2-methyl-4-(2,6,6-trimethyl-2-cyclohexen-1-yl)butanal, 2-methylundecanal, nonanal, cis-6-nonenal, octanal, phenylacetaldehyde, 2-phenylpropionaldehyde, 3-phenylpropionaldehyde, propionaldehyde, p-tolylacetaldehyde, tridecanal, 2,4,6-trimethyl-3-cyclohexen-1-carbaldehyde, 2,6,10-trimethyl-9-undecanal, 7-undecenal, 8-undecenal, 9-undecenal, 10-undecenal, valeraldehyde, acetanisole, 1'-acetonaphthone, 2'-acetonaphthone, acetone, acetophenone, 2-acetoxy-2,5-dimethyl-3(2H)furanone, 2-acetylcyclopentanone, 4-acetyl-1,1-dimethyl-6-t-butylindan, 7-acetyl-1,1,3,4,4,6-hexamethylindan, 2-acetyl-2-thiazoline, 6-acetyl-1,1,2,4,4,7-hexamethyl tetralin, allyl α-ionone, benzylideneacetone, 2,3-butanedione, 2-sec-butylcyclohexanone, 5-t-butyl-3,5-dinitro-2,6-dimethylacetophenone, butyrophenone, camphor, 2-decanone, 3-decanone, 3-decen-2-one, dihydrocarvone, dihydro-β-ionone, dihydrojasmone, 4,5-dihydro-3(2H)-thiophenone, 2',4'-dimethylacetophenone, 3,4-dimethyl-1,2-cyclopentadione, 3,5-dimethyl-1,2-cyclopentadione, 2,6-dimethyl-4-heptanone, 1,3-diphenyl-2-propanone, 4-(1-ethoxyvinyl)-3,3,5,5-tetramethylcyclohexanone, p-ethylacetophenone, ethyl vinyl ketone, geranylacetone, 2,3-heptanedione, 2-heptanone, 3-heptanone, 4heptanone, 3,4-hexanedione, 3-hexanone, 4-hexen-3-one, 2-hexylidene cyclopentanone, α-ionone, β-ionone, 4-isobutyl-2,6-dimethyl-3,5-dinitroacetophenone, isophorone, 6-isopropyldecahydro-2-naphthone, cis-jasmone, livescone, 4-methoxyacetophenone, 4-(p-methoxyphenyl)-2-butanone, 4'-methylacetophenone, 3-methyl-1,2-cyclohexanedione, 3-methyl-2-cyclohexen-1-one, 2-(2-(4-methyl-3-cylcohexen-1-yl)propyl)cyclopentanone, 3-methyl-2-cyclopenten-1-one, methyl dihydrojasmonate, methyl ethyl ketone, 2-methyl-3-heptanone, 5-methyl-2-hepten-4-one, 6-methyl-5-hepten-2-one, 5-methyl-α-ionone, 1-(2-methyl-5-isopropyl-2-cyclohexenyl)-1-propanone, 4-methyl-2-pentanone, 3-methyl-2-(2-pentenyl)-2-cyclopenten-1-one, 4-methyl-1-phenyl-2-pentanone, 2-methyltetrahydrofuran-3-one, 2-methyltetrahydrothiophen-3-one, 2-nonanone, 3-nonanone, 2-octanone, 3-octanone, 1-octen-3-one, 3-octen-2-one, 4-oxoisophorone, 2-pentadecanone, 2,3-pentanedione, 2-pentanone, 3-pentanone, 3-penten-2-one, 1-phenyl-1,2-propandione, propiophenone, pulegone, 2-tridecanone, 2,2,6-trimethylcyclohexanone, 4-(2,6,6-trimethyl-2-cylcohexen-1-yl)-3-methyl-3-buten-2-one, 2-undecanone, and 6-undecanone.

13. The active ingredient-releasing cyclic siloxane of claim 6 wherein RF has the formula $(R^1O)_a(R^2O)_b(R^3O)_c(R^4)_d(R^5)_e SiR^U$ with $R^U$ a $C_2$-$C_{40}$ divalent hydrocarbon radical and $R^4$ and $R^5$ independently selected from the group consisting of monovalent hydrocarbon radicals having from one to forty carbon atoms, the subscript a has a value ranging from 1 to 3 and the subscripts b, c, d, and e have values ranging from 0 to 2 subject to the limitation that a+b+c+d+e=3, where each $R^1O$, $R^2O$ and $R^3O$ are independently selected from the group of conjugate bases consisting of conjugate bases derived from the group of conjugate bases derived from the group of carbonyl active ingredients having the structure:

$$R^7-C(R^8)=C(O-)-R^9$$

where
$R^7$, $R^8$, and $R^9$ are each independently selected from the group consisting of hydrogen and monovalent hydrocarbon radicals having from one to one hundred carbon atoms.

14. The active ingredient-releasing cyclic siloxane of claim 13 wherein the carbonyl active ingredients are fragrant carbonyl active ingredients.

15. The active ingredient-releasing cyclic siloxane of claim 14 where the fragrant carbonyl active ingredients are selected from the group consisting of 4-acetoxy-3-pentyl-tetrahydropyran, allyl cinnamate, allyl 2-ethylbutyrate, allyl cyclohexanepropionate, allyl heptanoate, allyl hexanoate, allyl isovalerate, allyl nonanoate, allyl octanoate, allyl phenoxyacetate, allyl phenylacetate, allyl propionate, α-amylcinnamyl acetate, amyl octanoate, anisyl acetate, anisylphenyl acetate, benzyl acetate, benzyl acetoacetate, benzyl butyrate, benzyl cinnamate, benzyl isobutyrate, benzyl isovalerate, benzyl phenylacetate, benzyl propionate, bornyl acetate, bornyl isovalerate, bornyl valerate, butyl acetate, butyl butyrate, butyl butyryllactate, 4-t-butylcyclohexyl acetate, butyl heptanoate, butyl hexanoate, butyl isobutyrate, butyl isovalerate, butyl laurate, butyl propionate, butyl stearate, 3-butylidenephthalide, butyl 2-methylbutyrate, butyl 10-undeceneoate, γ-butyrolactone, carvyl acetate, carvyl propionate, caryophyllene acetate, cedryl acetate, trans-cinnamyl acetate, trans-cinnamyl butyrate, cinnamyl cinnamate, cinnamyl isobutyrate, citronellyl acetate, citronellyl butyrate, citronellyl isobutyrate, citronellyl propionate, citronellyl valerate, cyclohexaneethyl acetate, cyclohexyl acetate, cyclohexyl butyrate, cyclohexyl isovalerate, cyclohexyl propionate, δ-decalactone, ε-decalactone, γ-decalactone, 4-decanolide, decyl acetate, decyl butyrate, decyl propionate, diethyl malonate, diethyl sebacate, diethyl succinate, dihydrocarvyl acetate, dihydrocoumarin, dihydromyrcenyl acetate, dihydro-nor-dicyclopentadienyl acetate, dihydroterpinyl acetate, 3,7-dimethyl-1,6-octadien-3-yl acetate, 3,7-dimethyl-1,6-octadien-3-yl propionate, 3,7-dimethyloctan-3-yl acetate, α,α-dimethylphenethyl acetate, α,α-dimethylphenethyl butyrate, 6,10-dimethyl-5,9-undecadien-2-yl acetate, δ-dodecalactone, ε-dodecalactone, γ-dodecalactone, ethyl acetate, ethyl acetoacetate, ethyl 6-acetoxyhexanoate, ethyl 2-acetyl-3-phenylpropionate, ethyl benzoylacetate, 2-ethylbutyl acetate, ethyl butyrate, ethyl cinnamate, ethyl cyclohexanepropionate, ethyl decanoate, ethylene brassylate, ethyl 2-ethyl-6,6-dimethyl-2-cyclohexenecarboxylate, ethyl 2,3- epoxybutyrate, ethyl 2-methyl-4-penteneoate, ethyl heptanoate, ethyl hexanoate, ethyl trans-3-hexenoate, 2-ethylhexyl acetate, ethyl isobutyrate, ethyl isovalerate, ethyl laurate, ethyl 2-mercaptopropionate, ethyl 3-mercaptopropionate, ethyl 2-methylbutyrate, ethyl 2-methylpentanoate, ethyl (methylthio)acetate, ethyl myristate, ethyl nonanoate, ethyl octanoate, ethyl palmitate, ethyl phenylacetate, ethyl 3-phenylpropionate, ethyl 3-phenyl-2,3-epoxybutyrate, ethyl 3-phenylpropionate, ethyl propionate, ethyl stearate, ethyl 2,3,6,6-tetramethyl-2-cyclohexencarboxylate, ethyl (p-tolyloxy)acetate, ethyl undecanoate, ethyl valerate, eugenyl acetate, fenchyl acetate, geranyl acetate, geranyl butyrate, geranyl phenylacetate, geranyl propionate, guaiacyl phenylacetate, guaicwood acetate, γ-heptalactone, heptyl acetate, heptyl butyrate, heptyl isobutyrate, ω-6-hexadecenlactone, δ-hexylactone, γ-hexylactone, 3-hexenyl acetate, cis-3-hexenyl 2-methylbutanoate, cis-3-hexenyl cis-3-hexenoate, cis-3-hexenyl phenylacetate, trans-2-hexenyl acetate, hexyl acetate, hexyl butyrate, hexyl hexanoate, hexyl isobutyrate, hexyl propionate, hexyl 2-methylbutanoate, hexyl 3-methylbutanoate, hexyl phenylacetate, isoamyl acetate, isoamyl acetoacetate, isoamyl butyrate, isoamyl cinnamate, isoamyl hexanoate, isoamyl isobutyrate, isoamyl isovalerate, isoamyl laurate, isoamyl nonanoate, isoamyl octanoate, isoamyl phenylacetate, isoamyl propionate, isobornyl acetate, isobornyl propionate, isobutyl acetate, isobutyl butyrate, isobutyl cinnamate, isobutyl hexanoate, isobutyl isobutyrate, isobutyl 2-methylbutyrate, isobutyl propionate, isoeugenyl acetate, isopropyl cinnamate, isobutyl phenylacetate, isopropyl acetate, isopropyl butyrate, isopropyl isobutyrate, isopropyl myristate, isopropyl palmitate, isopropyl phenylacetate, lauryl acetate, linalyl acetate, linalyl butyrate, linalyl isovalerate, menthalactone, menthyl acetate, menthyl cyclohexanecarboxylate, menthyl isovalerate, 4-methoxybenzyl acetate, 4-methoxybenzyl propionate, 2-methoxyphenyl acetate, 2-methoxy-4-(1-propenyl)phenyl acetate, methyl acetate, α-methylbenzyl acetate, α-methylbenzyl butyrate, α-methylbenzyl propionate, 2-methylbutyl acetate, 2-methylbutyl butyrate, 2-methylbutyl isovalerate, 3-methylbutyl 2-methylbutanoate, 2-methylbutyl 2-methylbutanoate, methyl p-t-butylphenylacetate, methyl butyrate, methyl cinnamate, methyl decanoate, methyl heptanoate, methyl hexanoate, methyl isobutyrate, methyl isovalerate, methyl laurate, methyl N-2-methyl-3-(4-t-butylphenylpropylidene) anthranilate, methyl (methylthio)acetate, methyl 2-(methylthio) propionate, methyl myristate, methyl nonanoate, methyl octanoate, methyl palmitate, 4-(4-methyl-3-pentenyl)-3-cyclohexenylmethyl acetate, methyl 2-methylbutyrate, 2-methyl-6-methylen-7-octen-2-yl acetate, methyl 4-methylvalerate, methyl 2-methylpentanoate, methyl phenoxyacetate, 4-methylphenyl phenylacetate, 2-methyl-3-phenylpropan-2-yl acetate, methyl 3-phenylpropionate, methyl propionate, 2-methylpropyl phenylacetate, methyl phenylacetate, 2-methyl-3-phenylpropan-2-yl acetate, methyl stearate, methyl (p-tolyloxy)acetate, methyl 9-undecenoate, methyl valerate, myrtenyl acetate, neryl acetate, neryl butyrate, neryl isobutyrate, δ-nonalactone, γ-nonalactone, 1,3-nonanediol diacetate, nonyl acetate, nopyl acetate, octahydrocoumarin, γ-octalactone, 1-octen-3-yl acetate, 1-octen-3-yl butyrate, octyl acetate, octyl butyrate, octyl isobutyrate, octyl isovalerate, octyl octanoate, octyl propionate, oxacycloheptadec-10-en-2-one, ω-pentadecalactone, pentyl acetate, pentyl butyrate, pentyl hexanoate, pentyl octanoate, phenethyl acetate, phenethyl butyrate, phenethyl cinnamate, phenethyl hexanoate, phenethyl isobutyrate, phenethyl isovalerate, phenethyl 2-methylbutyrate, phenethyl 2-methylbutyrate, phenethyl 2-methylpropionate, phenethyl octanoate, phenethyl phenylacetate, phenethyl propionate, phenoxyethyl propionate, 2-phenoxyethyl 2-methylpropionate, 3-phenyl-2-propenyl propionate, 3-phenylpropyl acetate, 2-phenylpropyl butyrate, 2-phenylpropyl isobutyrate, 2-phenylpropyl isovalerate, piperonyl acetate, piperonyl isobutyrate, prenyl acetate, propyl acetate, propyl butyrate, propyl heptanoate, propyl hexanoate, 3-propylidenephthalide, propyl isobutyrate, propyl propionate, propyl phenylacetate, sucrose octaacetate, terpinyl acetate, terpinyl butyrate, terpinyl isobutyrate, terpinyl propionate, δ-nonalactone, tetrahydrofurfuryl acetate, tetrahydrofurfuryl butyrate, tetrahydrofurfuryl propionate, tetrahydrohnalyl acetate, 2,6,6,8-tetramethyl-tricyclo[5.3.1.0 (1.5)]udecan-8-yl acetate, p-tolyl acetate, p-tolyl isobutyrate, p-tolyl phenylacetate, triacetin, tributyl acetylcitrate, tributyrin, tripropionin, 3,5,5-trimethylhexyl acetate, δ-undecalactone, γ-undecalactone, γ-valerolactone, vanillin acetate, vanillyl isobutyrate, 1-vinyl-2-(1-methylpropyl)cyclohexyl acetate, whiskey lactone, butyraldehyde, citronellal, decanal, cis-4-decenal, trans-4-decenal, 2,4-dimethyl-3-cyclohexen-1-carbaldehyde, 2,6-dimethyl-5-heptenal, 3,7-dimethyloctanal, 2-ethylbutyraldehyde, glutaric dialdehyde, heptanal, cis-4-heptenal, hexanal, hydrocinnamaldehyde, isobutyraldehyde, 3-(p-isopropylphenyl)propionaldehyde, isovaleraldehyde, lauric aldehyde, 2-methylbutyraldehyde, 2-methyl-3-(p-isopropylphenyl)propionaldehyde, 2-methylpentanal, 4-(4-methyl-3-pentenyl)-3-cyclohexen-1-carbaldehyde, 4-methylphenylacetaldehyde, 3-(methylthio)butanal, 2-methyl-4-(2,6,6-trimethyl-2-cyclohexen-1-yl)butanal, 2-methylundecanal, nonanal, cis-6-nonenal, octanal, phenylacetaldehyde, 2-phenylpropionaldehyde, 3-phenylpropionaldehyde, propionaldehyde, p-tolylacetaldehyde, tridecanal, 2,4,6-trimethyl-3-cyclohexen-1-carbaldehyde, 2,6,10-trimethyl-9-undecanal, 7-undecenal, 8-undecenal, 9-undecenal, 10-undecenal, valeraldehyde, acetanisole, 1'-acetonaphthone, 2'-acetonaphthone, acetone, acetophenone, 2-acetoxy-2,5-dimethyl-3(2H)furanone, 2-acetylcyclopentanone, 4-acetyl-1,1-dimethyl-6-t-butylindan, 7-acetyl-1,1,3,4,4,6-hexamethylindan, 2-acetyl-2-thiazoline, 6-acetyl-1,1,2,4,4,7-hexamethyl tetralin, allyl α-ionone, benzylideneacetone, 2,3-butanedione, 2-sec-butylcyclohexanone, 5-t-butyl-3,5-dinitro-2,6-dimethylacetophenone, butyrophenone, camphor, 2-decanone, 3-decanone, 3-decen-2-one, dihydrocarvone, dihydro-β-ionone, dihydrojasmone, 4,5-dihydro-3(2H)-thiophenone, 2',4'-dimethylacetophenone, 3,4-dimethyl-1,2-cyclopentadione, 3,5-dimethyl-1,2-cyclopentadione, 2,6-dimethyl-4-heptanone, 1,3-diphenyl-2-propanone, 4-(1-ethoxyvinyl)-3,3,5,5-tetramethylcyclohexanone, p-ethylacetophenone, ethyl vinyl ketone, geranylacetone, 2,3-heptanedione, 2-heptanone, 3-heptanone, 4-heptanone, 3,4-hexanedione, 3-hexanone, 4-hexen-3-one, 2-hexylidene cyclopentanone, α-ionone, β-ionone, 4-isobutyl-2,6-dimethyl-3,5-dinitroacetophenone, isophorone, 6-isopropyldecahydro-2-naphthone, cis-jasmone, livescone, 4-methoxyacetophenone, 4-(p-methoxyphenyl)-2-butanone, 4'-methylacetophenone, 3-methyl-1,2-cyclohexanedione, 3-methyl-2-cyclohexen-1-one, 2-(2-(4-methyl-3-cylcohexen-1-yl)propyl)cyclopentanone, 3-methyl-2-cyclopenten-1-one, methyl dihydrojasmonate, methyl ethyl ketone, 2-methyl-3-heptanone, 5-methyl-2-hepten-4-one, 6-methyl-5-hepten-2-one, 5-methyl-α-ionone, 1-(2-methyl-5-isopropyl-2-cyclohexenyl)-1-propanone, 4-methyl-2-pentanone, 3-methyl-2-(2-pentenyl)-2-cyclopenten-1-one, 4-methyl-1-phenyl-2-pentanone, 2-methyltetrahydrofuran-3-one, 2-methyltetrahydrothiophen-3-one, 2-nonanone, 3-nonanone, 2-octanone, 3-octanone, 1-octen-3-one, 3-octen-2-one, 4-oxoisophorone, 2-pentadecanone, 2,3-pentanedione, 2-pentanone, 3-pentanone, 3-penten-2- one, 1-phenyl-1,2-propandione, propiophenone, pulegone, 2-tridecanone, 2,2,6-trimethylcyclohexanone, 4-(2,6,6-trimethyl-2-cylcohexen-1-yl)-3-methyl-3-buten-2-one, 2-undecanone, and 6-undecanone.

16. A composition comprising the active ingredient releasing siloxane of claim 1.

17. A composition comprising the active ingredient releasing siloxane of claim 2.

18. A composition comprising the active ingredient releasing siloxane of claim 6.

19. A composition comprising the active ingredient releasing siloxane of claim 10.

20. A composition comprising the active ingredient releasing siloxane of claim 13.

21. A composition consisting essentially of the active ingredient releasing siloxane of claim 1.

* * * * *